United States Patent
Tsuruta et al.

(10) Patent No.: US 11,160,442 B2
(45) Date of Patent: Nov. 2, 2021

(54) ENDOSCOPE APPARATUS

(71) Applicant: OLYMPUS CORPORATION, Tokyo (JP)

(72) Inventors: Misa Tsuruta, Hino (JP); Toshiaki Watanabe, Hino (JP); Yuichi Takeuchi, Fuchu (JP); Hiroki Uchiyama, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 692 days.

(21) Appl. No.: 15/922,159

(22) Filed: Mar. 15, 2018

(65) Prior Publication Data

US 2018/0199801 A1 Jul. 19, 2018

Related U.S. Application Data

(63) Continuation of application No. PCT/JP2016/061147, filed on Apr. 5, 2016.

(30) Foreign Application Priority Data

Sep. 18, 2015 (JP) .............................. JP2015-185489

(51) Int. Cl.
   *A61B 1/04* (2006.01)
   *A61B 1/06* (2006.01)
   (Continued)

(52) U.S. Cl.
   CPC .......... *A61B 1/043* (2013.01); *A61B 1/00186* (2013.01); *A61B 1/045* (2013.01);
   (Continued)

(58) Field of Classification Search
   CPC ... A61B 1/043; A61B 1/0638; A61B 1/00186; G02B 21/06
   See application file for complete search history.

(56) References Cited

U.S. PATENT DOCUMENTS

2006/0052710 A1 3/2006 Miura et al.
2007/0285771 A1* 12/2007 Nakaoka .............. A61B 5/0086
                                                              359/389
(Continued)

FOREIGN PATENT DOCUMENTS

EP      1795111 A1    6/2007
EP      2122331       11/2009
(Continued)

OTHER PUBLICATIONS

International Search Report dated Jun. 21, 2016 issued in PCT/JP2016/061147.

*Primary Examiner* — Alexandra L Newton
*Assistant Examiner* — Rynae Boler
(74) *Attorney, Agent, or Firm* — Scully, Scott, Murphy & Presser, P.C.

(57) ABSTRACT

An endoscope apparatus includes a spectroscopic section disposed on an optical axis of return light from an object irradiated with visible light, first excitation light and second excitation light including a longer wavelength than a wavelength of the first excitation light and configured to separate and emit the light of a second wavelength band other than light of a first wavelength band, a first excitation light cut filter configured to block a wavelength band of one of the first excitation light and the second excitation light included in the return light, and a second excitation light cut filter configured to block a wavelength band of another excitation light of the first excitation light and the second excitation light and a wavelength band of the visible light.

8 Claims, 13 Drawing Sheets

(51) Int. Cl.
  *G02B 26/00* (2006.01)
  *G02B 23/24* (2006.01)
  *A61B 1/045* (2006.01)
  *A61B 1/00* (2006.01)
  *A61B 5/00* (2006.01)
  *G01N 21/64* (2006.01)

(52) U.S. Cl.
  CPC .......... *A61B 1/0638* (2013.01); *A61B 1/0646* (2013.01); *A61B 1/0661* (2013.01); *A61B 5/0071* (2013.01); *G02B 23/2469* (2013.01); *G02B 23/2484* (2013.01); *G02B 26/008* (2013.01); *A61B 1/00009* (2013.01); *G01N 21/6456* (2013.01)

(56) References Cited

U.S. PATENT DOCUMENTS

| | | |
|---|---|---|
| 2008/0027286 A1 | 1/2008 | Xie |
| 2009/0236541 A1 | 9/2009 | Lomnes et al. |
| 2010/0036203 A1* | 2/2010 | Nakaoka ............. A61B 5/0084 600/178 |
| 2011/0001061 A1 | 1/2011 | Ishihara |
| 2012/0265014 A1 | 10/2012 | Matsubara et al. |

FOREIGN PATENT DOCUMENTS

| | | |
|---|---|---|
| JP | 2006-075189 A | 3/2006 |
| JP | 2006-102481 A | 4/2006 |
| JP | 2008-148791 A | 7/2008 |
| JP | 2009-226067 A | 10/2009 |
| JP | 2011-188929 A | 9/2011 |
| JP | 2011-224127 A | 11/2011 |
| WO | WO 2006/028023 A1 | 3/2006 |
| WO | WO 2008/072444 A1 | 6/2008 |
| WO | WO 2008/089545 A1 | 7/2008 |
| WO | WO 2009/119369 A1 | 10/2009 |
| WO | WO 2009/120416 A1 | 10/2009 |
| WO | WO 2015/023990 A1 | 2/2015 |

\* cited by examiner

ENDOSCOPE APPARATUS

CROSS REFERENCE TO RELATED APPLICATION

This application is a continuation application of PCT/JP2016/061147 filed on Apr. 5, 2016 and claims benefit of Japanese Application No. 2015-185489 filed in Japan on Sep. 18, 2015, the entire contents of which are incorporated herein by this reference.

BACKGROUND OF THE INVENTION

1. Field of the Invention

The present invention relates to an endoscope apparatus suitable for use in white light observation and fluorescence observation.

2. Description of the Related Art

In recent years, cancer diagnostic technologies using molecular target agents are becoming a focus of attention. This is a technique that sprays or injects a fluorescent probe (fluorescent agent) targeting biological proteins specifically expressed in a cancer cell into a target region of a living body and then determines presence or absence of the cancer based on fluorescence emitted from the target region. This technique is useful in early detection of a cancer in the digestive tract field.

With an endoscope apparatus, diagnosis can be performed based on fluorescence observation using the technique. That is, the endoscope apparatus performs presence diagnosis or qualitative diagnosis of malignancy of a cancer by irradiating an object with excitation light from a light source apparatus and capturing fluorescence from a fluorescent agent accumulated in the cancer.

A plurality of fluorescent agents can also be administered for diagnosis. It is possible to perform fluorescence observation in a plurality of wavelength bands corresponding to a type of each fluorescent agent. It is possible to obtain fluorescence corresponding to each excitation light by emitting excitation light of a plurality of wavelength bands corresponding to respective fluorescent agents from the light source apparatus and irradiating the object with the excitation light. Fluorescence is generally generated on a longer wavelength side than the wavelength of excitation light. Since a reflected light component of the excitation light reflected from the object is greater than a level of fluorescence obtained from the excitation light, it is necessary to use an excitation light cut filter for blocking passage of the excitation light in order to perform fluorescence observation.

An apparatus configured to simultaneously perform normal observation (white light observation) through irradiation with white light and fluorescence observation is being developed. European Patent Application Publication No. 2122331 Specification (hereinafter referred to as "Document 1") discloses a technique for an apparatus configured to simultaneously perform white light observation and fluorescence observation and cut excitation light beams in a plurality of wavelength bands using one excitation light cut filter. The apparatus described in Document 1 separates white light, excitation light and fluorescence from each other using a beam splitter and further cuts the excitation light beams of the plurality of wavelength bands using an excitation light cut filter. The apparatus thus enables white light observation and fluorescence observation using a plurality of fluorescent beams.

Note that since the level of the reflected white light is relatively higher than the level of the fluorescence, the beam splitter cannot always totally separate the white light.

SUMMARY OF THE INVENTION

An endoscope apparatus according to an aspect of the present invention includes a spectroscopic section disposed on an optical axis of return light from an object irradiated with visible light, first excitation light and second excitation light including a longer wavelength than a wavelength of the first excitation light and configured to separate light of a first wavelength band including a wavelength band of the visible light, make the light of the first wavelength band incident on an image pickup device for white light observation, and separate and emit light of a second wavelength band other than the first wavelength band, a first excitation light cut filter disposed on the optical axis between the object and the spectroscopic section and configured to block a wavelength band of one of the first excitation light and the second excitation light included in the return light, and emit the return light of a wavelength band other than the blocked wavelength band to the spectroscopic section, and a second excitation light cut filter disposed on an optical axis of the light of the second wavelength band emitted from the spectroscopic section and configured to block a wavelength band of another excitation light of the first excitation light and the second excitation light and the wavelength band of the visible light, pass light of a wavelength band of first fluorescence excited by the first excitation light and light of a wavelength band of second fluorescence excited by the second excitation light, and emit light of a wavelength band other than the blocked wavelength bands to an image pickup device for fluorescence observation.

An endoscope apparatus according to another aspect of the present invention includes a spectroscopic section disposed on an optical axis of return light from an object and configured to separate light of a first wavelength band including a wavelength band of visible light and make the light of the first wavelength band incident on an image pickup device for white light observation, and separate light of a second wavelength band other than the first wavelength band and emit the light of the second wavelength band in a direction different from the direction of the optical axis, a first excitation light cut filter disposed on the optical axis between the object and the spectroscopic section and configured to block a wavelength band of at least one of first excitation light and second excitation light included in the return light, and emit the return light of a wavelength band other than the blocked wavelength band to the spectroscopic section, and a second excitation light cut filter disposed on an optical axis of the light of the second wavelength band emitted from the spectroscopic section and configured to block a wavelength band of excitation light not blocked by the first excitation light cut filter of the first excitation light and the second excitation light, and the wavelength band of the visible light and emit light of a wavelength band other than the blocked wavelength band to an image pickup device for fluorescence observation, in which the second excitation light includes a longer wavelength than a wavelength of the first excitation light, the first excitation light and first fluorescence generated from the object based on the first excitation light are included in the wavelength band of the visible light, the second excitation light and second fluorescence generated from the object based on the second excitation light include longer wavelengths than a wavelength of the visible light, the first excitation light cut filter blocks the wavelength bands of the first excitation light and the second excitation light, and the second excitation light cut filter passes a longer wavelength band than a wavelength band of the first fluorescence and a wavelength band of the second fluorescence.

An endoscope apparatus according to a further aspect of the present invention includes a spectroscopic section disposed on an optical axis of return light from an object and configured to separate light of a first wavelength band including a wavelength band of visible light and make the light of the first wavelength band incident on an image pickup device for white light observation, and separate light of a second wavelength band other than the first wavelength band and emit the light of the second wavelength band in a direction different from the direction of the optical axis, a first excitation light cut filter disposed on the optical axis between the object and the spectroscopic section and configured to block a wavelength band of at least one of first excitation light and second excitation light included in the return light, and emit the return light of a wavelength band other than the blocked wavelength band to the spectroscopic section, and a second excitation light cut filter disposed on an optical axis of the light of the second wavelength band emitted from the spectroscopic section and configured to block a wavelength band of excitation light not blocked by the first excitation light cut filter of the first excitation light and the second excitation light, and a wavelength band of the visible light, and emit light of a wavelength band other than the blocked wavelength bands to an image pickup device for fluorescence observation, in which the second excitation light includes a longer wavelength than a wavelength of the first excitation light, the first excitation light and first fluorescence generated from the object based on the first excitation light are included in a wavelength band of the visible light, the second excitation light and second fluorescence generated from the object based on the second excitation light include a longer wavelength than a wavelength of the visible light, the first excitation light cut filter blocks the wavelength bands of the first excitation light, and the second excitation light cut filter passes a longer wavelength band than a wavelength band of the first fluorescence and a wavelength band of the second fluorescence.

An endoscope apparatus according to a still further aspect of the present invention includes a spectroscopic section disposed on an optical axis of return light from an object and configured to separate light of a first wavelength band including a wavelength band of visible light and make the light of the first wavelength band incident on an image pickup device for white light observation, and separate light of a second wavelength band other than the first wavelength band and emit the light of the second wavelength band in a direction different from the direction of the optical axis, a first excitation light cut filter disposed on the optical axis between the object and the spectroscopic section and configured to block a wavelength band of at least one of first excitation light and second excitation light included in the return light, and emit the return light of a wavelength band other than the blocked wavelength band to the spectroscopic section, and a second excitation light cut filter disposed on an optical axis of the light of the second wavelength band emitted from the spectroscopic section and configured to block a wavelength band of excitation light not blocked by the first excitation light cut filter of the first excitation light and the second excitation light and a wavelength band of the visible light, and emit light of a wavelength band other than the blocked wavelength band to an image pickup device for fluorescence observation, in which the second excitation light includes a longer wavelength than a wavelength of the first excitation light, the first excitation light is included in the wavelength band of the visible light, first fluorescence generated from the object based on the first excitation light, the second excitation light and second fluorescence generated from the object based on the second excitation light include longer wavelengths than a wavelength of the visible light, the first excitation light cut filter blocks the wavelength band of the first excitation light, and the second excitation light cut filter passes a longer wavelength band than a wavelength band of the first fluorescence and a wavelength band of the second fluorescence.

DETAILED DESCRIPTION OF THE PREFERRED EMBODIMENTS

Hereinafter, embodiments of the present invention will be described in detail with reference to the accompanying drawings.

First Embodiment

Figure 1A:
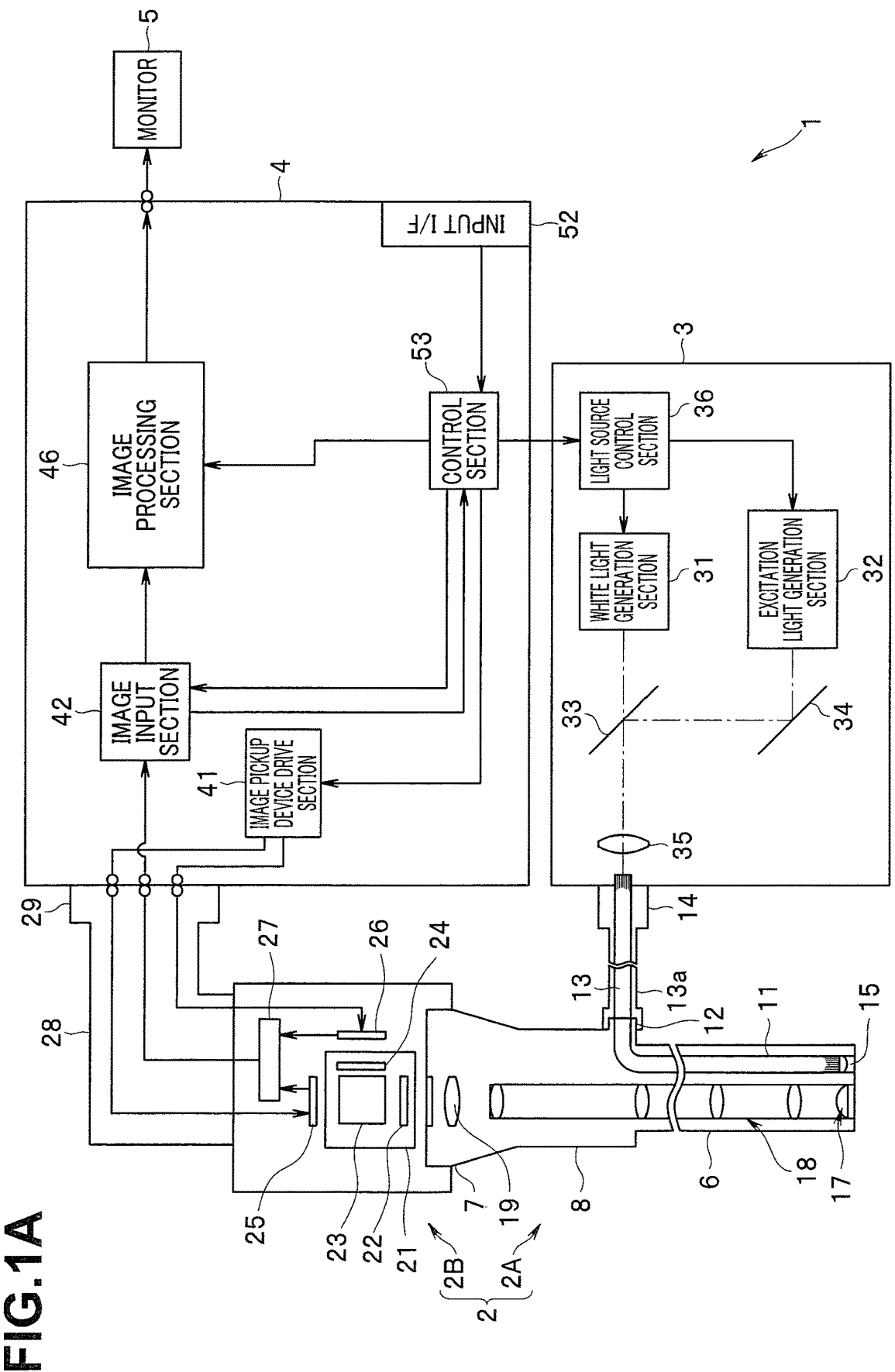
FIG. 1A is a block diagram illustrating an endoscope system including an endoscope apparatus according to a first embodiment of the present invention.

FIG. 1A is a block diagram illustrating an endoscope system including an endoscope apparatus according to a first embodiment of the present invention.

As shown in FIG. 1A, an endoscope system 1 includes an endoscope apparatus 2 which is inserted into a subject and configured to pick up an image of an object such as living tissue in the subject and output the picked-up image as an image pickup signal, a light source apparatus 3 configured to supply illumination light for illuminating the object to the endoscope apparatus 2, a video processor 4 configured to apply signal processing to the image pickup signal outputted from the endoscope apparatus 2 to thereby generate and output an observation image or the like and a monitor 5 configured to display the observation image or the like outputted from the video processor 4 on a screen.

The endoscope apparatus 2 includes an optical viewing tube 2A provided with an elongated insertion portion 6 and a camera unit 2B attachable/detachable to/from an eyepiece section 7 of the optical viewing tube 2A. The optical viewing tube 2A is constructed of the elongated insertion portion 6 inserted into the subject, a grasping portion 8 provided at a proximal end portion of the insertion portion 6 and the eyepiece section 7 provided at a proximal end portion of the grasping portion 8.

The light source apparatus 3 is constructed of a white light generation section 31, an excitation light generation section 32, dichroic mirrors 33 and 34, a condensing lens 35 and a light source control section 36.

The white light generation section 31 is constructed of, for example, a xenon lamp that emits wideband white light or an LED. The white light generation section 31 is configured so as to be switched between a lighting-on state and a lighting-off state according to control by the light source control section 36. The white light generation section 31 is configured to generate white light with a light quantity according to control by the light source control section 36.

Figure 1B:
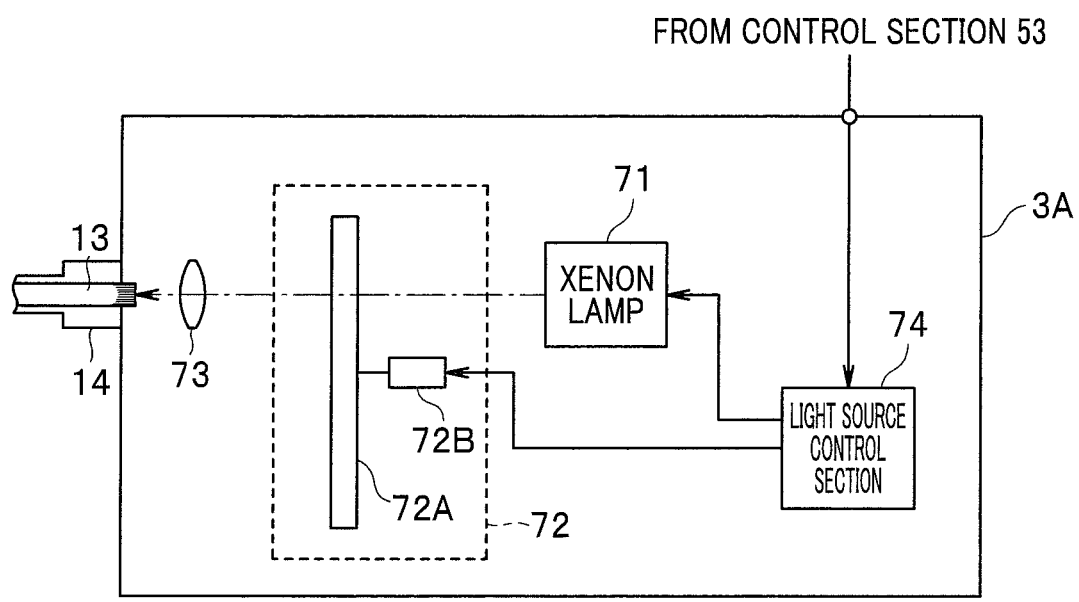
FIG. 1B is a block diagram illustrating another example of a light source apparatus.

Note that the endoscope system 1 may also be configured using a light source apparatus 3A having a configuration as shown in FIG. 1B instead of the light source apparatus 3 in the present embodiment.

As shown in FIG. 1B, the light source apparatus 3A is constructed of a xenon lamp 71, a filter switching apparatus 72, a condensing lens 73 and a light source control section 74. The xenon lamp 71 is configured so as to emit, for example, BL light which is wideband light including visible light to an infrared band (two excitation light wavelength bands). Furthermore, the xenon lamp 71 is configured so as to be switched between a lighting-on state and a lighting-off state according to control by the light source control section 74. The xenon lamp 71 is configured to generate BL light with a light quantity according to control by the light source control section 74 in a lighting-on state.

The filter switching apparatus 72 is constructed of a rotary filter 72A provided so as to vertically cross an optical path of light emitted from the xenon lamp 71 and a motor 72B configured to be driven to rotate according to control by the light source control section 74 to thereby switch the filter to be inserted into the optical path of the light emitted from the xenon lamp 71 to one of respective filters of the rotary filter 72A.

Figure 1C:
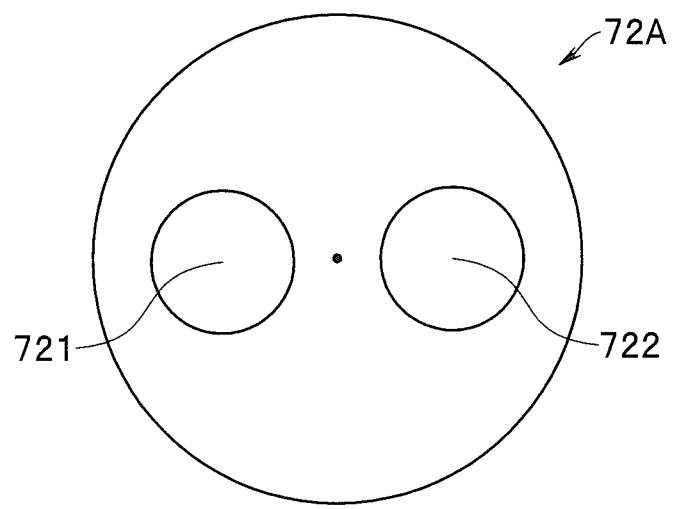
FIG. 1C is an explanatory diagram illustrating a rotary filter adopted for the light source apparatus in FIG. 1B.

FIG. 1C is an explanatory diagram illustrating an example of a configuration of the rotary filter provided in the light source apparatus in FIG. 1B. The rotary filter 72A is formed into, for example, a disk shape. As shown in, for example, FIG. 1C, the rotary filter 72A is provided with a white light observation filter 721 and a fluorescence observation filter 722. The white light observation filter 721 is formed so as to have an optical characteristic of, for example, transmitting light included in a visible light band and shielding light included in a wavelength band other than the visible light band.

The fluorescence observation filter 722 is formed so as to have an optical characteristic of, for example, transmitting light included in a predetermined wavelength band used for fluorescence observation and shielding light included in a wavelength band other than the predetermined wavelength band. Note that the fluorescence observation filter 722 may also be configured to be able to transmit a plurality of wavelength bands as the predetermined wavelength band used for fluorescence observation.

That is, the filter switching apparatus 72 is configured to be able to drive the motor 72B to rotate according to control by the light source control circuit 74, interpose either the white light observation filter 721 or the fluorescence observation filter 722 on the optical path of the light emitted from the xenon lamp 71 and cause the other filter different from the one filter to retract from the optical path.

The condensing lens 73 is configured to condense light made incident through the filter switching apparatus 72 and emit the light to a light guide 13. The light source control section 74 is configured to perform control on the xenon lamp 71 and the filter switching apparatus 72 based on an illumination control signal outputted from a control section 53 of the video processor 4.

More specifically, the light source control section 74 is configured, for example, upon detecting that an observation mode of the endoscope system 1 is set to a white light observation mode, to perform control on the xenon lamp 71 to generate BL light with a predetermined light quantity and perform control on the motor 72B of the filter switching apparatus 72 so as to interpose the white light observation filter 721 on the optical path of the light emitted from the xenon lamp 71 based on the illumination control signal outputted from the control section 53. The light source control section 74 is also configured, for example, upon detecting that an observation mode of the endoscope system 1 is set to a fluorescence observation mode, to perform control on the xenon lamp 71 to generate BL light with a predetermined light quantity and perform control on the motor 72B of the filter switching apparatus 72 so as to interpose the fluorescence observation filter 722 on the optical path of the light emitted from the xenon lamp 71 based on the illumination control signal outputted from the control section 53.

The excitation light generation section 32 is provided with a plurality of LEDs or the like configured to respectively emit light beams (excitation light beams) of a plurality of predetermined wavelength bands including excitation wavelengths of a plurality of fluorescent agents administered into the subject respectively. The excitation light generation section 32 is also configured so as to be switched between a lighting-on state and a lighting-off state according to control by the light source control section 36. The excitation light generation section 32 is also configured to generate excitation light with a light quantity according to control by the light source control section 36.

The dichroic mirror 33 is formed so as to have an optical characteristic of, for example, transmitting the white light emitted from the white light generation section 31 toward the condensing lens 35 side and reflecting excitation light emitted from the excitation light generation section 32 toward the condensing lens 35 side.

The dichroic mirror 34 is formed so as to have an optical characteristic of, for example, reflecting the excitation light emitted from the excitation light generation section 32 toward the dichroic mirror 33 side.

The condensing lens 35 is configured to condense the light made incident through the dichroic mirror 33 and emit the condensed light into the light guide 13.

The light source control section 36 is configured to perform control on the white light generation section 31 and the excitation light generation section 32 according to an illumination control signal outputted from the video processor 4.

A light guide 11 for transmitting illumination light supplied via a cable 13a is inserted into the insertion portion 6 of the optical viewing tube 2A. An emission end portion of the light guide 11 is disposed in the vicinity of an illumination lens 15 at the distal end portion of the insertion portion 6. An incidence end portion of the light guide 11 is disposed at a light guide base 12 provided in the grasping portion 8.

The light guide 13 for transmitting illumination light supplied from the light source apparatus 3 is inserted into the cable 13a. A connection member (not shown) that can be detachably attached to the light guide base 12 is provided at one end of the cable 13a. A light guide connector 14 that can be detachably attached to the light source apparatus 3 is provided at the other end of the cable 13a.

An illumination window (not shown) provided with the illumination lens 15 for emitting illumination light transmitted by the light guide 11 to outside and an objective window (not shown) provided with an objective lens 17 for acquiring an optical image corresponding to light made incident from outside are provided adjacent to each other on a distal end face of the insertion portion 6.

Relay lenses 18 for transmitting an optical image obtained by the objective lens 17 to the eyepiece section 7 are provided inside the insertion portion 6. An eyepiece lens 19 to make an optical image transmitted by the relay lenses 18 observable to the naked eye is provided inside the eyepiece section 7.

The camera unit 2B includes an optical section 21, image pickup devices 25 and 26 and a signal processing circuit 27. The optical section 21 is configured to extract white light for generating a white light image from return light of an object made incident through the eyepiece lens 19 and also extract fluorescence for generating a fluorescence image from the return light of the object made incident through the eyepiece lens 19. The white light extracted by the optical section 21 is made incident on an image pickup surface of the image pickup device 25 configured to generate a white light image and the fluorescence extracted by the optical section 21 is made incident on an image pickup surface of the image pickup device 26 configured to generate a fluorescence image.

The image pickup device 25 is constructed of a color CCD, on an image pickup surface of which a primary color system or a complementary color system color filter is provided. The image pickup device 25 is configured to perform image pickup operation in response to an image pickup device drive signal outputted from the video processor 4. The image pickup device 25 is configured to pick up an image of white light formed by the optical section 21 and generate and output a white light image corresponding to the picked-up image of white light.

The image pickup device 26 is constructed of, for example, a high sensitivity monochrome CCD. Furthermore, the image pickup device 26 is configured to perform image pickup operation in response to an image pickup device drive signal outputted from the video processor 4. The image pickup device 26 is configured to pick up an image of fluorescence formed by the optical section 21 and generate and output a fluorescence image in response to the picked-up image of fluorescence.

The optical section 21 is constructed of an excitation light cut filter 22 which is a first excitation light cut filter, an excitation light cut filter 24 which is a second excitation light cut filter and a beam splitter 23 which is a spectroscopic section. The excitation light cut filters 22 and 24 are provided with a spectral characteristic of cutting a wavelength band of excitation light emitted from the light source apparatus 3. The beam splitter 23 receives light from the eyepiece lens 19 via the excitation light cut filter 22 and splits the incident light into a white light band and other bands. The beam splitter 23 is configured to pass the separated light of the white light band and guide the light to the image pickup device 25, reflect the light of wavelength bands other than the passed wavelength band and guide the light to the image pickup device 26 via the excitation light cut filter 24.

Note that in the present embodiment, as will be described later, characteristics of the excitation light cut filters 22 and 24 and the beam splitter 23 are set according to the wavelength bands of the excitation light and the fluorescence as appropriate.

The signal processing circuit 27 is configured to apply predetermined signal processing such as correlated double sampling processing, gain adjustment processing and A/D conversion processing to the white light image outputted from the image pickup device 25 and the fluorescence image outputted from the image pickup device 26 and output the fluorescence image and the white light image subjected to the predetermined signal processing to the video processor 4 via a cable 28.

An image pickup device drive section 41 of the video processor 4 is constructed of, for example, a driver circuit. The image pickup device drive section 41 is configured to generate and output an image pickup device drive signal according to control by the control section 53. An image input section 42 is provided with, for example, a buffer memory and configured to store images sequentially outputted from the signal processing circuit 27 of the camera unit 2B corresponding to one frame and output the stored images for one frame at a time to an image processing section 46. Furthermore, the image input section 42 is configured to output stored white light images for one frame at a time to the image processing section 46 according to control by the control section 53. The image input section 42 is configured to output stored fluorescence images for one frame at a time to the image processing section 46 according to control by the control section 53.

The image processing section 46 is provided with an image processing circuit for performing, for example, predetermined image processing. Furthermore, the image processing section 46 is configured to apply predetermined image processing to the white light images sequentially outputted from the image input section 42 for one frame at a time according to control by the control section 53, thereby generate a white light image and output the white light image generated to the monitor 5. Furthermore, the image processing section 46 is configured to apply predetermined image processing to the fluorescence images sequentially outputted from the image input section 42 for one frame at a time according to control by the control section 53, thereby generate a fluorescence image and output the fluorescence image generated to the monitor 5.

The control section 53 can be constructed of a processor such as a CPU. The control section 53 may also be configured to read a program stored in a memory (not shown) and control each section according to the read program. An input I/F 52 receives operation signals from one or more input apparatuses capable of giving instructions according to a user's operation. The control section 53 may also be configured to control each section based on an operation signal inputted via the input I/F 52. Furthermore, the control section 53 is configured to generate an illumination control signal for emitting illumination light corresponding to an observation mode of the endoscope system 1 and output the illumination control signal to the light source control section 36.

In the present embodiment, the control section 53 is configured to be able to control the light source apparatus 3 and control each section in a simultaneous observation mode in which white light observation through irradiation with white light and fluorescence observation through fluorescence emitted from two types of fluorescence pigments are simultaneously performed. That is, in the simultaneous observation mode, the control section 53 controls the light source control section 36 so as to generate white light and two types of excitation light for fluorescence of two types of fluorescence pigments. When the light source apparatus 3A in FIG. 1B is adopted as the light source apparatus, the control section 53 is configured to be able to control each section so as to implement white light observation through irradiation with white light and fluorescence observation through fluorescence emitted from the two types of fluorescence pigments while switching the observations in a time-division manner.

Note that at least one of the two types of fluorescence acquired in the present embodiment is assumed to have a longer wavelength than that of the wavelength of visible light.

The wavelength band of excitation light may or may not exist within the wavelength band of white light (wavelength band of visible light). When the wavelength band of excitation light exists within the wavelength band of white light, in generating a white light image, a return light component of the excitation light may be used to create the white light image. Note that as will be described later, a white light image may be generated using light not including some wavelength band components of visible light depending on the wavelength bands of excitation light and fluorescence, and therefore, light not including some wavelength band components of visible light may also be described as white light in the following description.

The following three patterns A to C are available as white light image generation patterns in the image processing section 46 depending on the relationship between the wavelength band of excitation light and the wavelength band of white light. In the present embodiment, patterns A and B of the three patterns A to C are applicable. Note that of the two types of excitation light, excitation light having a longer wavelength is referred to as "L excitation light" and excitation light having a shorter wavelength is referred to as "S excitation light."

A . . . No return light component of S excitation light and L excitation light is used to create a white light image.

B . . . Only one of return light components of S excitation light and L excitation light is used to create a white light image.

C . . . Both return light components of S excitation light and L excitation light are used to create a white light image.

Furthermore, the following four patterns a to d may be considered as a pattern A. Note that of the two types of fluorescence, fluorescence having a longer wavelength is referred to as "L fluorescence" and fluorescence having a shorter wavelength is referred to as "S fluorescence."

A-a . . . Both S fluorescence and L fluorescence have a longer wavelength than that of visible light.

A-b . . . S fluorescence has a blue color (B) and L fluorescence has a longer wavelength than that of visible light.

A-c . . . S fluorescence has a green color (G) and L fluorescence has a longer wavelength than that of visible light.

A-d . . . S fluorescence has a red color (R) and L fluorescence has a longer wavelength than that of visible light.

Four patterns a to d may be likewise considered for pattern B.

B-a . . . Both S fluorescence and L fluorescence have a longer wavelength than that of the wavelength of visible light.

B-b . . . S fluorescence has a blue color (B) and L fluorescence has a longer wavelength than that of visible light.

B-c . . . S fluorescence has a green color (G) and L fluorescence has a longer wavelength than that of visible light.

B-d . . . S fluorescence has a red color (R) and L fluorescence has a longer wavelength than that of visible light.

In the present embodiment, for the aforementioned patterns A-a to A-d and patterns B-a to B-d, it is possible to reliably separate the white light and two types of fluorescence using one beam splitter 23 and two types of excitation light cut filters 22 and 24 and acquire white light images and fluorescence images with high accuracy.

(Separation of White Light and Two Types of Fluorescence)

Next, a method of separating white light and two types of fluorescence using the optical section 21 in such a configuration will be described with reference to FIG. 2 to FIG. 11. FIG. 2, FIG. 4, FIG. 6, FIG. 8 and FIG. 10 are explanatory diagrams illustrating a relationship between settings of the excitation light cut filters 22 and 24 in the examples of patterns A-a, B-d, A-b to A-d and a variation of light emitted from the light source apparatus 3 up to the image pickup devices 25 and 26. FIG. 3, FIG. 5, FIG. 7, FIG. 9 and FIG. 11 are explanatory diagrams illustrating filter control of light in the examples of patterns A-a, B-d, A-b to A-d.

An excitation light cut filter is generally configured to cut a wavelength component of excitation light and pass a wavelength component of fluorescence. Such an excitation light cut filter is configured by laminating a plurality of films. Note that examples of a film formation method include ion-assisted vapor deposition. A filter characteristic is designed such that an OD (optical density) value which is a logarithm of a ratio between incident light and outgoing light increases. However, in order to obtain a high OD value, that is, to make the filter characteristic steep and reliably cause only fluorescence to pass, it is necessary to increase the number of films to be laminated.

Moreover, as proposed in Document 1, in order to cut excitation light of two wavelength bands using one excitation light cut filter, it is necessary to constitute a filter having two notches. To obtain a sufficient characteristic as a notch filter, more films need to be laminated and configured compared to a long pass filter or a short pass filter. Moreover, in the case of a double notch filter having two notches, the number of necessary films increases extremely compared to a single notch filter.

When the number of films laminated is extremely large, it is difficult to obtain a desired OD value or a wavelength characteristic due to an error in the film thickness. Moreover, when the number of films is large, the filter itself is likely to deform. For this reason, the proposal in Document 1 has a disadvantage that the manufacturing yield of an excitation light cut filter having a desired characteristic is extremely low.

The pattern A-a in the present embodiment allows the excitation light cut filters 22 and 24 to be constructed of a filter with one notch or with a long pass characteristic. Thus, in the case of the pattern A-a, it is possible to adopt a product with a relatively small number of films and high manufacturing yield as the excitation light cut filters 22 and 24.

(Pattern A-a)

Figure 2:
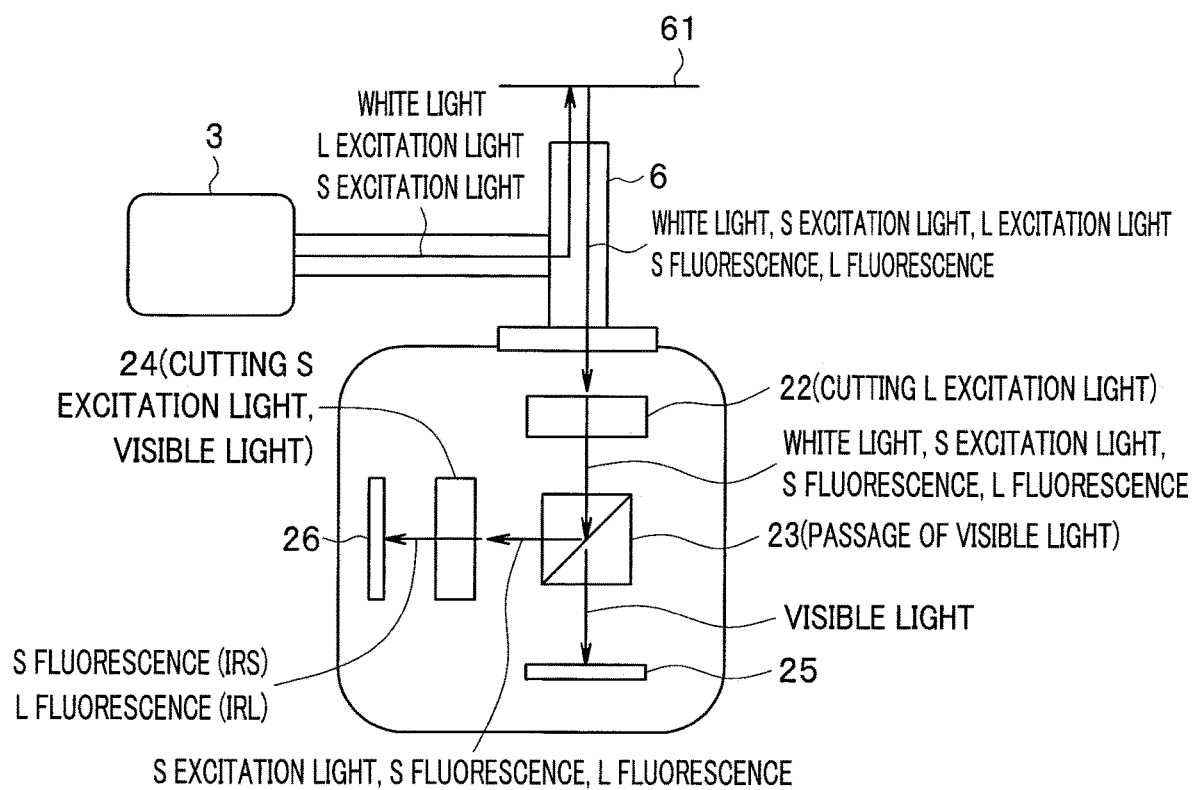
FIG. 2 is an explanatory diagram illustrating a relationship between settings of excitation light cut filters 22 and 24 in an example of a pattern A-a and a variation of light emitted from a light source apparatus 3 up to image pickup devices 25 and 26.
Figure 3:
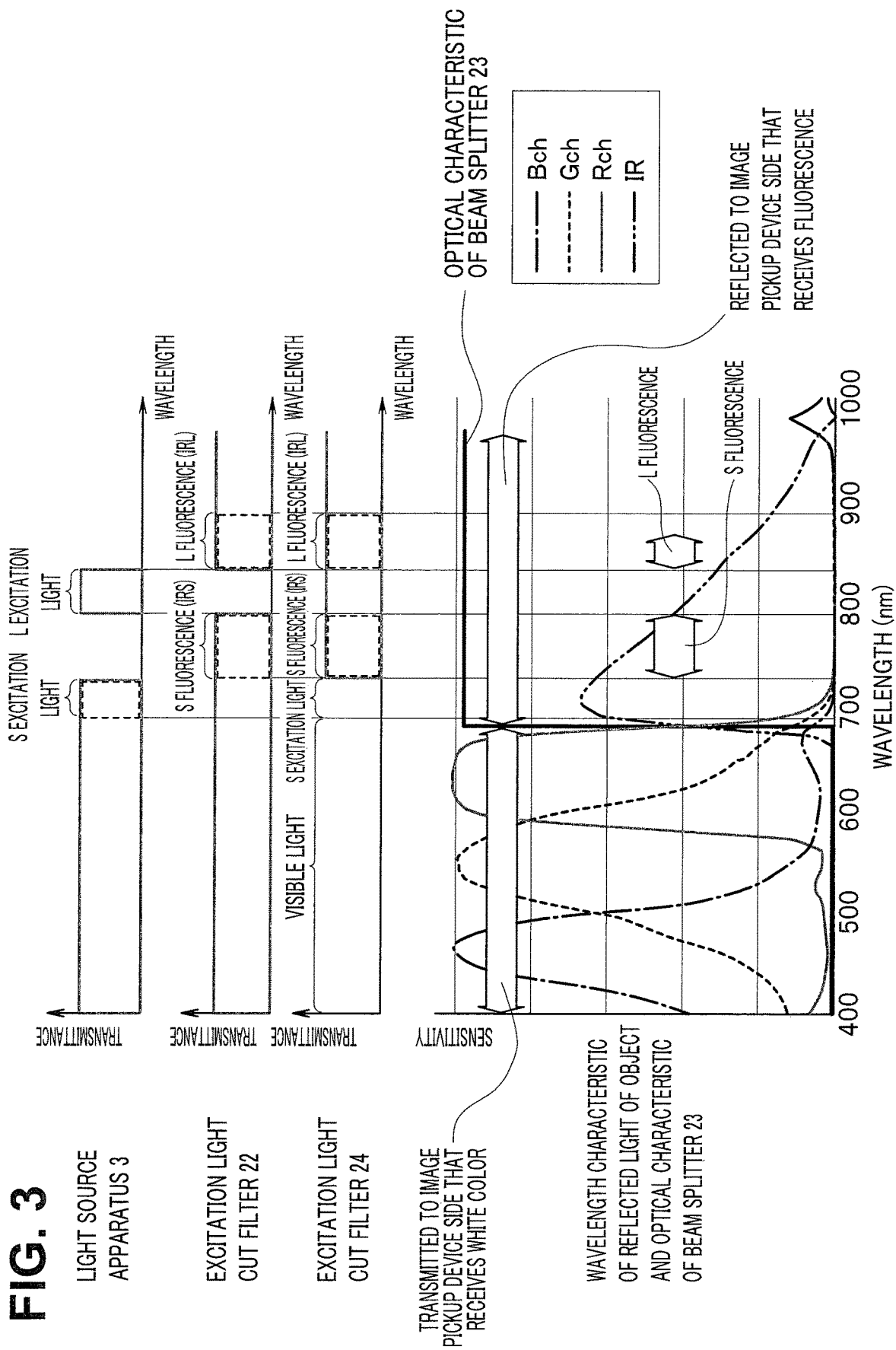
FIG. 3 is an explanatory diagram illustrating filter control of light in the example of the pattern A-a.

As shown in FIG. 2, in a simultaneous observation mode, the light source apparatus 3 emits light including white light, S excitation light and L excitation light. As shown in FIG. 3, in the pattern A-a, both S excitation light and L excitation light have a longer wavelength than that of visible light and the wavelength band of S excitation light is a band on the longer wavelength side contiguous to the wavelength band of visible light. Light from the light source apparatus 3 is transmitted to the light guide 11 of the insertion portion 6 and is radiated from the illumination lens 15 onto an object surface 61. The return light from the object surface 61 includes L fluorescence generated by L excitation light and S fluorescence generated by S excitation light in addition to white light and return light of L excitation light and S excitation light (hereinafter simply referred to as "white light, L excitation light and S excitation light").

Note that in the light source apparatus 3 in FIG. 3, thick lines show regions with a high transmittance in the excitation light cut filters 22 and 24. At the lower part in FIG. 3, a single-dot dashed line, a broken line, a solid line and a two-dot dashed line show sensitivity characteristics of a blue band (Bch), a green band (Gch), a red band (Rch) and a near-infrared band (IR) of the return light respectively. As shown in FIG. 3, S fluorescence (IRS) in a near-infrared band is generated on a longer wavelength side of S excitation light and L fluorescence (IRL) in the near-infrared band is generated on a longer wavelength side of L excitation light.

The return light from the object is made incident on the excitation light cut filter 22 of the optical section 21 via the eyepiece lens 19. In this case, the excitation light cut filter 22 is constructed of a notch filter having a notch characteristic in the wavelength band of L excitation light, removes the L excitation light component from the incident light and transmits wavelength bands other than the L excitation light wavelength band. In this case, light including white light, S excitation light and S fluorescence and L fluorescence passes through the excitation light cut filter 22 and is made incident on the beam splitter 23.

The beam splitter 23 passes the visible light band and reflects other bands as shown in FIG. 3. White light which is a visible light band is made incident on the image pickup device 25 in this way.

On the other hand, the beam splitter 23 changes the optical axis of light other than the visible light band by $_{90}$ degrees and emits the light to the excitation light cut filter 24. As shown in FIG. 3, in this case, the excitation light cut filter 24 is constructed of a long pass filter that cuts a wavelength band including visible light and S excitation light and passes other wavelength bands. That is, the light that passes through the excitation light cut filter 24 is a wavelength band of S fluorescence (near-infrared band (IRS) and a wavelength band of L fluorescence or higher (near-infrared band (IRL)). S fluorescence and L fluorescence are made incident on the image pickup device 26 in this way.

Thus, in the case of the pattern A-a, the excitation light cut filter 22 is constructed of a notch filter that cuts L excitation light having a longer wavelength than the wavelength band of visible light and the excitation light cut filter 24 is constructed of a long pass filter that cuts the shorter wavelength side than the wavelength band of S excitation light including the wavelength band of visible light. The technique in Document 1 or the like cuts two types of excitation light, and thus has to adopt double notch filters having a notch characteristic at two locations. In contrast, in the present embodiment, the excitation light cut filters 22 and 24 can be constructed of single notch filters or long pass filters. Therefore, each of the filters 22 and 24 can be constructed of a relatively small number of films and achieve relatively high yield.

If the excitation light cut filter 22 is constructed of a notch filter that cuts S excitation light, the excitation light cut filter 24 needs to cut L excitation light, and so the excitation light cut filter 24 also needs to be constructed of a notch filter that cuts L excitation light. In this case, the single notch filter can be constructed with a smaller number of films than the double notch filter, but the number of films is larger than the number of films of a long pass filter. For this reason, in the present embodiment, the excitation light cut filter 22 on which incident light is made incident first is constructed of a notch filter that cuts L excitation light and the excitation light cut filter 24 is constructed of a long pass filter that cuts the shorter wavelength side than the wavelength band of S excitation light including the visible light band. Thus, in the case of the excitation light cut filter 24 in particular, it is possible to sufficiently reduce the number of films and achieve high yield.

Light incident on the excitation light cut filter 24 is outgoing light of the beam splitter 23 that separates and reflects wavelength bands other than visible light, and the excitation light cut filter 24 is formed of a long pass filter that cuts a shorter wavelength side than the wavelength band of S excitation light including the visible light band, and it is thereby possible to cut visible light by both the beam splitter 23 and the excitation light cut filter 24. Since visible light is cut using the two filters, light from which the visible light (white light) component is fully removed is emitted from the excitation light cut filter 24. Thus, since no white light component is included in a fluorescence image obtained by the image pickup device 26, a high accuracy fluorescence image is obtained.

(Pattern B-d)

Figure 4:
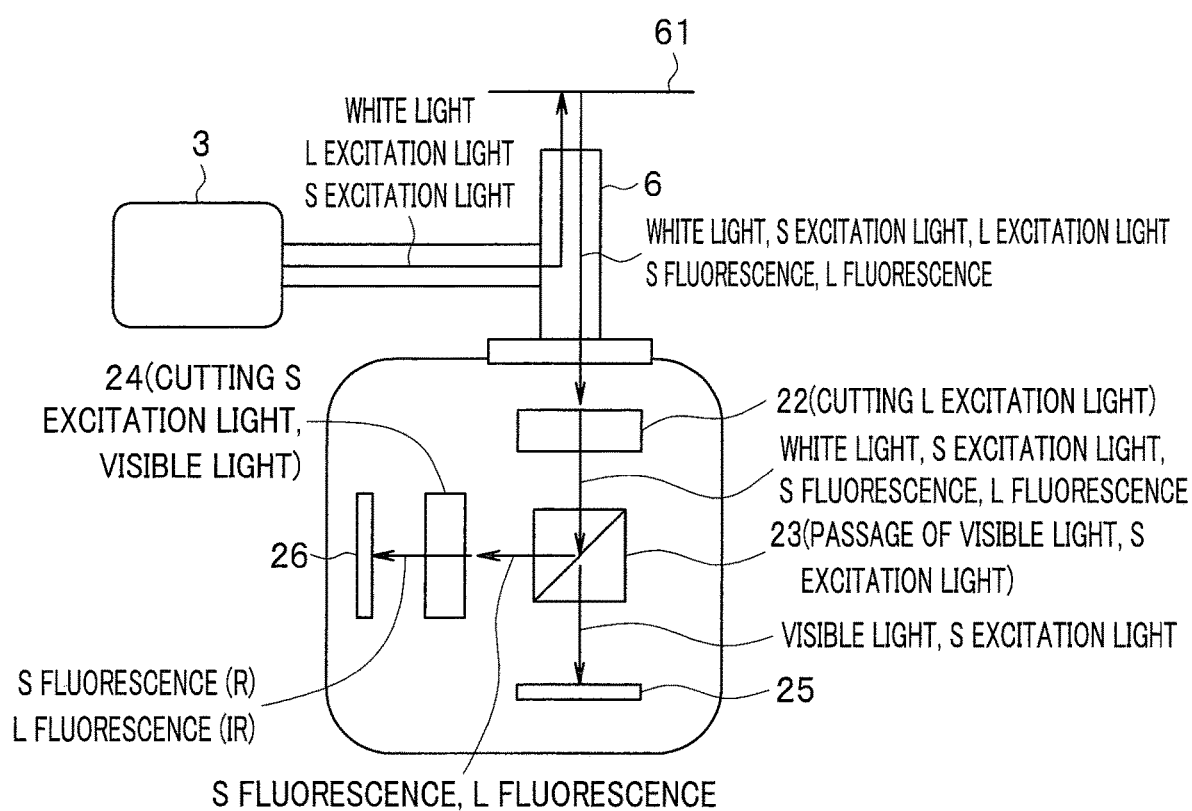
FIG. 4 is an explanatory diagram illustrating a relationship between settings of the excitation light cut filters 22 and 24 in an example of a pattern B-d and a variation of light emitted from the light source apparatus 3 up to the image pickup devices 25 and 26.
Figure 5:
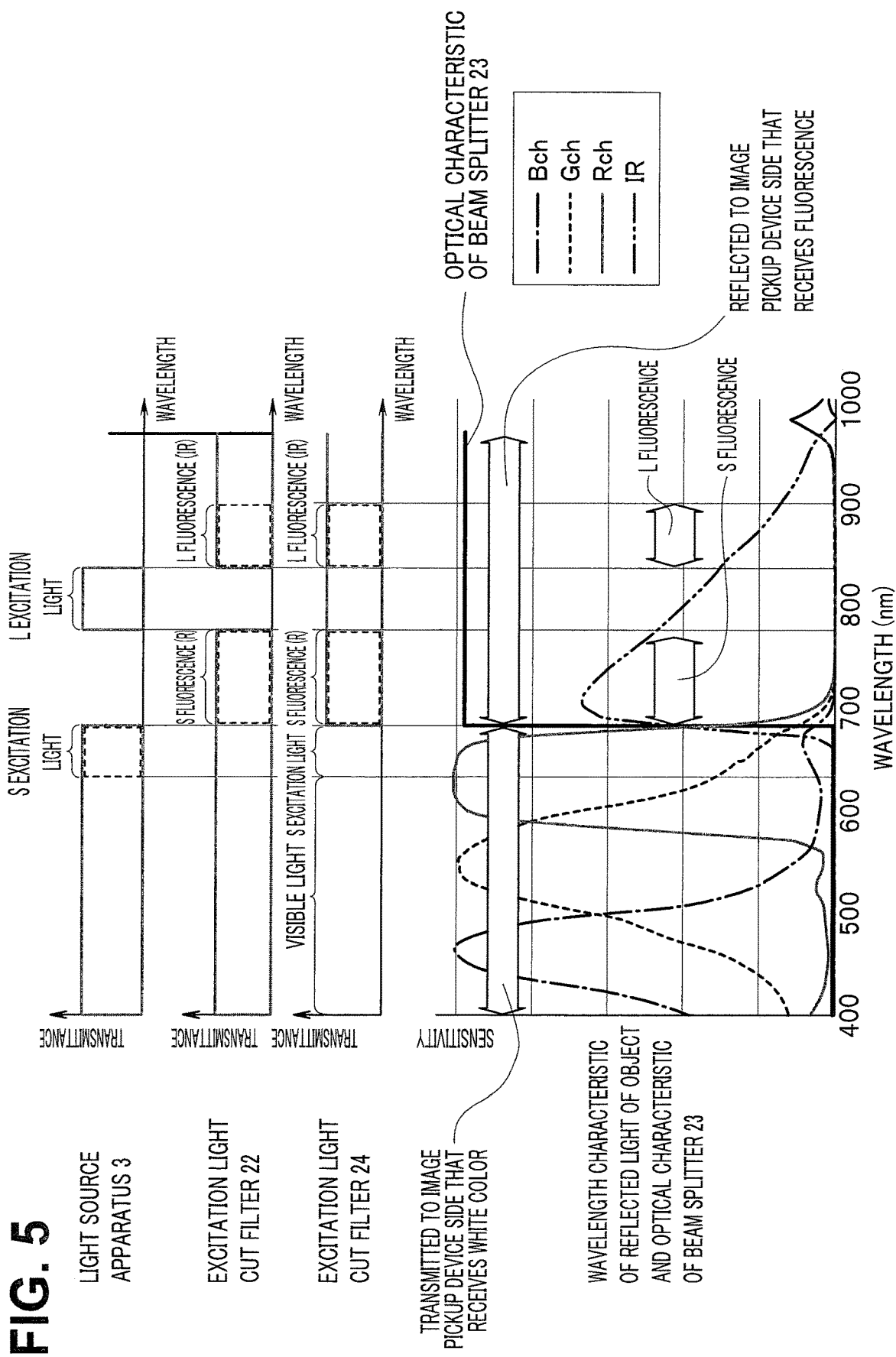
FIG. 5 is an explanatory diagram illustrating filter control of light in the example of the pattern B-d.

FIG. 4 and FIG. 5 are described using the same description method as in FIG. 2 and FIG. 3 respectively, and FIG. 4 and FIG. 5 are intended to describe light passing through the excitation light cut filters 22 and 24 and the beam splitter 23 in a pattern B-d. As shown in FIG. 5, in the pattern B-d, L excitation light has a longer wavelength than that of visible light and the wavelength band of S excitation light is a band on a longest wavelength side in the wavelength band of visible light. The return light from the object surface 61 includes white light, L excitation light and S excitation light, L fluorescence and S fluorescence. As shown in FIG. 5, red S fluorescence (R) is generated on the longer wavelength side of S excitation light and L fluorescence (IR) in the near-infrared band is generated on the longer wavelength side of L excitation light.

The return light from the object is made incident on the excitation light cut filter 22. In this case, the excitation light cut filter 22 is constructed of a notch filter having a notch characteristic in the wavelength band of L excitation light and thus removes an L excitation light component from the incident light and transmits wavelength bands other than the L excitation light wavelength band. In this case, light including white light, S excitation light, and L fluorescence and S fluorescence passes through the excitation light cut filter 22 and is made incident on the beam splitter 23.

As shown in FIG. 5, the beam splitter 23 passes the visible light wavelength band and the S excitation light wavelength band and reflects other bands. In this way, white light made up of visible light and the S excitation light wavelength band is made incident on the image pickup device 25.

On the other hand, the beam splitter 23 changes the optical axis of light other than visible light and the S excitation light wavelength band by 90 degrees and emits the light to the excitation light cut filter 24. As shown in FIG. 5, in this case, the excitation light cut filter 24 is constructed of a long pass filter that cuts a wavelength band including visible light and S excitation light and passes other wavelength bands. That is, the light that passes through the excitation light cut filter 24 is red S fluorescence (IR) and a wavelength band equal to or longer than L fluorescence (IR) of the near-infrared band. In this way, S fluorescence and L fluorescence are made incident on the image pickup device 26.

Thus, in the pattern B-d, the excitation light cut filter 22 is constructed of a notch filter that cuts L excitation light having a longer wavelength than the wavelength band of visible light and the excitation light cut filter 24 is constructed of a long pass filter that cuts the shorter wavelength side than the wavelength band of S excitation light including the wavelength band of visible light. Therefore, each of the filters 22 and 24 can be constructed with a relatively small number of films and can achieve relatively high yield.

In the pattern B-d, the excitation light cut filter 22 on which incident light is made incident first is also constructed of a notch filter that cuts L excitation light and the excitation light cut filter 24 is constructed of a long pass filter that cuts a shorter wavelength side than the wavelength band of S excitation light including the visible light band. Thus, the excitation light cut filter 24 in particular can sufficiently reduce the number of films and achieve high yield.

In the present embodiment, light incident on the excitation light cut filter 24 is outgoing light of the beam splitter 23 that separates and reflects wavelength bands other than visible light and S excitation light, and the excitation light cut filter 24 is constructed of a long pass filter that cuts a shorter wavelength side than the wavelength band of S excitation light including the visible light band so that visible light may be cut by both filters of the beam splitter 23 and the excitation light cut filter 24. Since visible light is cut by the two filters, the excitation light cut filter 24 emits light, the visible light (white light) component of which is sufficiently removed. In this way, the fluorescence image obtained by the image pickup device 26 includes no white light component, and so a high accuracy fluorescence image can be obtained.

(Pattern A-b)

Figure 6:
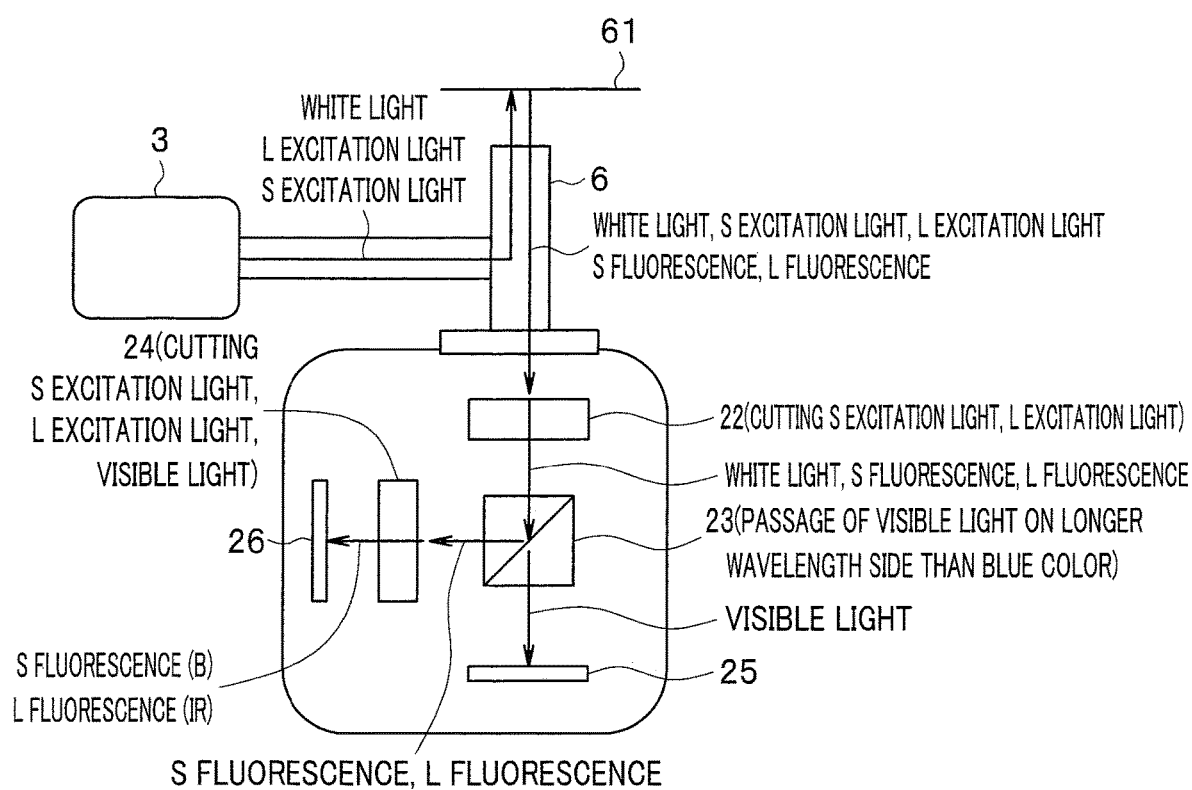
FIG. 6 is an explanatory diagram illustrating a relationship between settings of the excitation light cut filters 22 and 24 in an example of a pattern A-b and a variation of light emitted from the light source apparatus 3 up to the image pickup devices 25 and 26.
Figure 7:
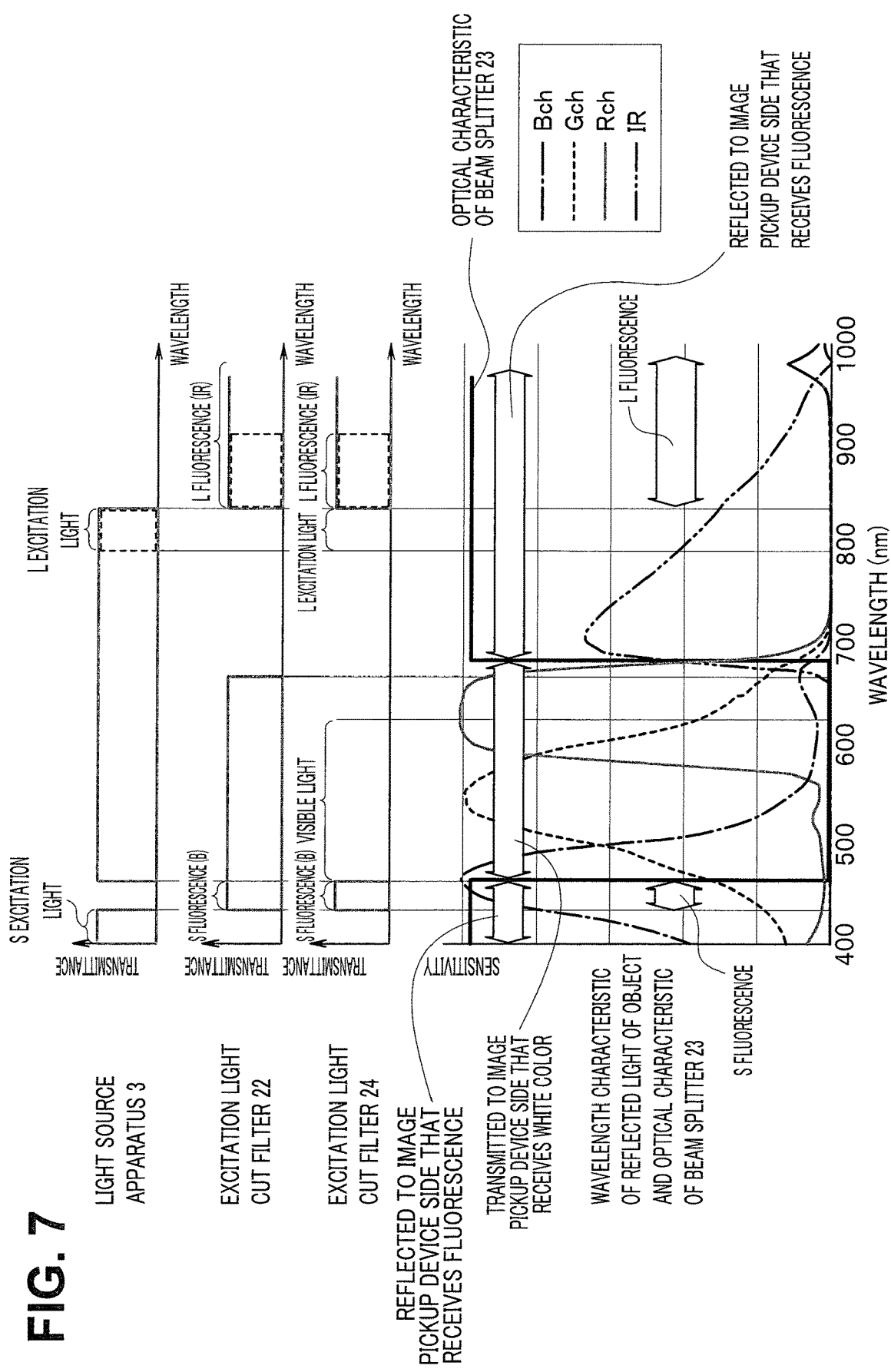
FIG. 7 is an explanatory diagram illustrating filter control of light in the example of the pattern A-b.

FIG. 6 and FIG. 7 are described using the same description method as in FIG. 2 and FIG. 3 respectively, and FIG. 6 and FIG. 7 are intended to describe light passing through the excitation light cut filters 22 and 24 and the beam splitter 23 in a pattern A-b. As shown in FIG. 7, in the pattern A-b, only L excitation light has a longer wavelength than that of visible light and the wavelength band of S excitation light is a band on a shortest wavelength side of the wavelength band of visible light. The return light from the object surface 61 includes white light, L excitation light and S excitation light, L fluorescence and S fluorescence. As shown in FIG. 7, blue S fluorescence (B) is generated on the longer wavelength side of S excitation light and L fluorescence (IR) in the near-infrared band is generated on the longer wavelength side of L excitation light.

The return light from the object is made incident on the excitation light cut filter 22. In this case, the excitation light cut filter 22 is constructed of a double notch filter having a notch characteristic in bands including the wavelength band of S excitation light and the wavelength band of L excitation light, and removes the S excitation light and L excitation light components from the incident light and passes other wavelength bands. Thus, in this case, the light including white light and L fluorescence and S fluorescence passes through the excitation light cut filter 22 and is made incident on the beam splitter 23.

As shown in FIG. 7, the beam splitter 23 passes the visible light wavelength band on a longer wavelength side than the blue color and reflects other bands. In this way, white light made up of visible light on the longer wavelength side than the blue color is made incident on the image pickup device 25.

On the other hand, the beam splitter 23 changes the optical axis of the light other than the wavelength band of visible light on a longer wavelength side than the blue color by 90 degrees and emits the light to the excitation light cut filter 24. As shown in FIG. 7, in this case, the excitation light cut filter 24 cuts the wavelength band including visible light, S excitation light and L excitation light and passes the wavelength band of S fluorescence (B) of the blue color, the wavelength band of L fluorescence (IR) of the near-infrared band, and a wavelength band on a longer wavelength side than L fluorescence (IR) of the near-infrared band. That is, the light that passes through the excitation light cut filter 24 is blue S fluorescence (B) and a wavelength band equal to or longer than L fluorescence (IR) of the near-infrared band. Thus, S fluorescence and L fluorescence are made incident on the image pickup device 26.

Thus, in the pattern A-b, the light incident on the excitation light cut filter 24 is outgoing light of the beam splitter 23 that separates and reflects the wavelength band other than visible light on a longer wavelength side than the blue color, and the light from which visible light is cut is made incident on the excitation light cut filter 24 from the beam splitter 23. Furthermore, the excitation light cut filter 24 is configured to pass only blue S fluorescence (B), L fluorescence (IR) of the near-infrared band, and a wavelength band having a longer wavelength than L fluorescence (IR) of the near-infrared band, and the excitation light cut filter 24 cuts visible light. Thus, visible light is cut by both filters of the beam splitter 23 and the excitation light cut filter 24, and the excitation light cut filter 24 emits light from which the visible light (white light) component is sufficiently removed. Thus, the fluorescence image obtained by the image pickup device 26 includes no white light component, and it is thereby possible to obtain a high accuracy fluorescence image.

(Pattern A-c)

Figure 8:
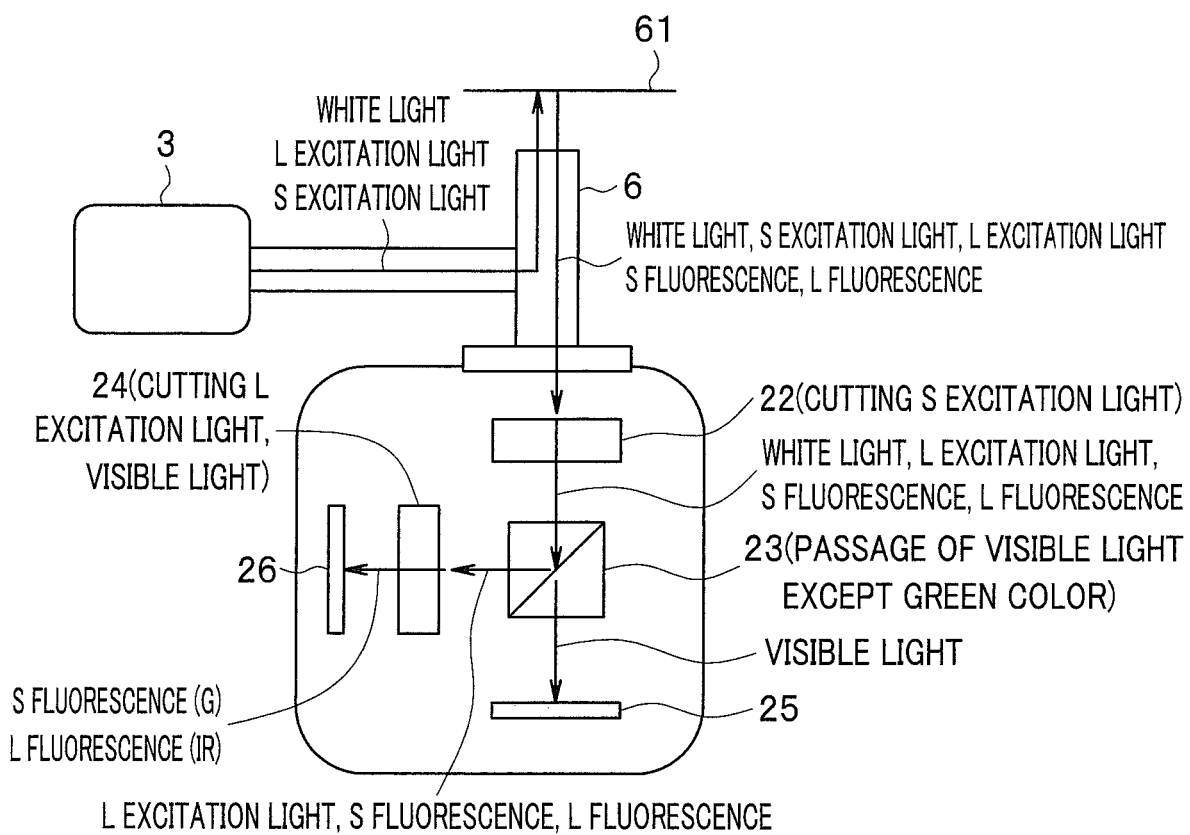
FIG. 8 is an explanatory diagram illustrating a relationship between settings of the excitation light cut filters 22 and 24 in an example of a pattern A-c and a variation of light emitted from the light source apparatus 3 up to the image pickup devices 25 and 26.
Figure 9:
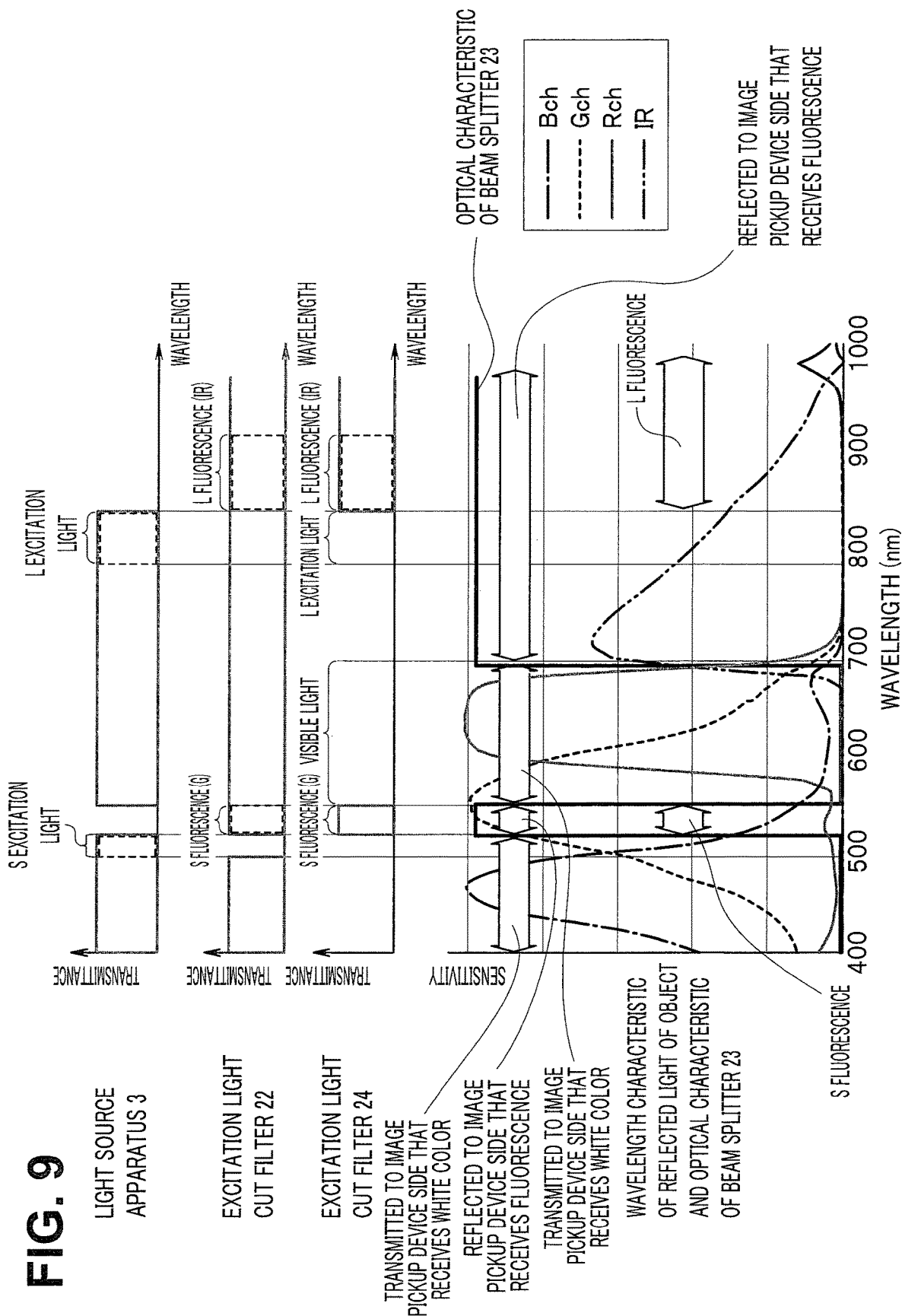
FIG. 9 is an explanatory diagram illustrating filter control of light in the example of the pattern A-c.

FIG. 8 and FIG. 9 are described using the same description method as in FIG. 2 and FIG. 3 respectively, and FIG. 8 and FIG. 9 are intended to describe light passing through the excitation light cut filters 22 and 24 and the beam splitter 23 in a pattern A-c. As shown in FIG. 9, in the pattern A-c, only the L excitation light has a longer wavelength than that of visible light and the wavelength band of S excitation light is a band on a shorter wavelength side of the green band in the wavelength band of visible light. The return light from the object surface 61 includes white light, L excitation light and S excitation light, L fluorescence and S fluorescence. As shown in FIG. 9, green S fluorescence (G) is generated on the longer wavelength side of S excitation light and L fluorescence (IR) in the near-infrared band is generated on the longer wavelength side of L excitation light.

The return light from the object is made incident on the excitation light cut filter 22. In this case, the excitation light cut filter 22 is constructed of a single notch filter having a notch characteristic in a wavelength band of S excitation light, and removes the S excitation light component from the incident light and passes other wavelength bands. Thus, in this case, the light including white light, L excitation light and L fluorescence and S fluorescence passes through the excitation light cut filter 22 and is made incident on the beam splitter 23.

As shown in FIG. 9, the beam splitter 23 passes a wavelength band of visible light except the wavelength band of green color and reflects other bands. White light made up of visible light except the wavelength band of green color is made incident on the image pickup device 25 in this way.

On the other hand, the beam splitter 23 changes the optical axis of the light other than the wavelength band of visible light except the green color by 90 degrees and emits the light to the excitation light cut filter 24. As shown in FIG. 9, in this case, the excitation light cut filter 24 cuts a wavelength band including visible light and L excitation light and passes the wavelength band of S fluorescence (G of the green color), the wavelength band of L fluorescence (IR) of the near-infrared band, and the wavelength band on a longer wavelength side than L fluorescence (IR) of the near-infrared band. That is, the light that passes through the excitation light cut filter 24 is green S fluorescence (G) and a wavelength band equal to or longer than L fluorescence (IR) of the near-infrared band. Thus, S fluorescence and L fluorescence are made incident on the image pickup device 26.

Thus, in the pattern A-c, the light incident on the excitation light cut filter 24 is outgoing light of the beam splitter 23 that separates and reflects wavelength bands other than visible light except the green color, and the light from which visible light is cut is made incident on the excitation light cut filter 24 from the beam splitter 23. Furthermore, the excitation light cut filter 24 is configured to pass only green S fluorescence (G), L fluorescence (IR) of the near-infrared band, and a wavelength band having a longer wavelength than L fluorescence (IR) of the near-infrared band, and the excitation light cut filter 24 cuts visible light. Thus, visible light is cut by both filters of the beam splitter 23 and the excitation light cut filter 24, and the excitation light cut filter 24 emits light from which the visible light (white light) component is sufficiently removed. Thus, the fluorescence image obtained by the image pickup device 26 includes no white light component, and it is thereby possible to obtain a high accuracy fluorescence image.

(Pattern A-d)

Figure 10:
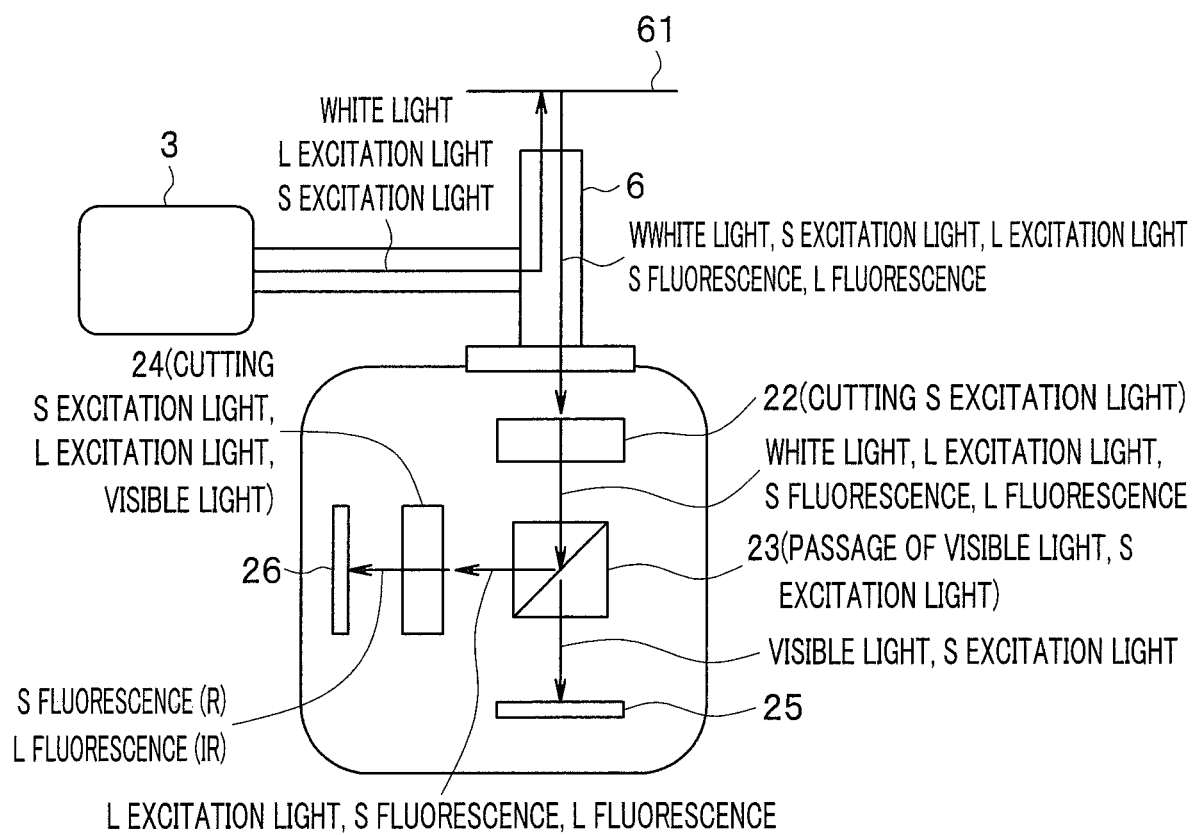
FIG. 10 is an explanatory diagram illustrating a relationship between settings of the excitation light cut filters 22 and 24 in an example of a pattern A-d and a variation of light emitted from the light source apparatus 3 up to the image pickup devices 25 and 26.
Figure 11:
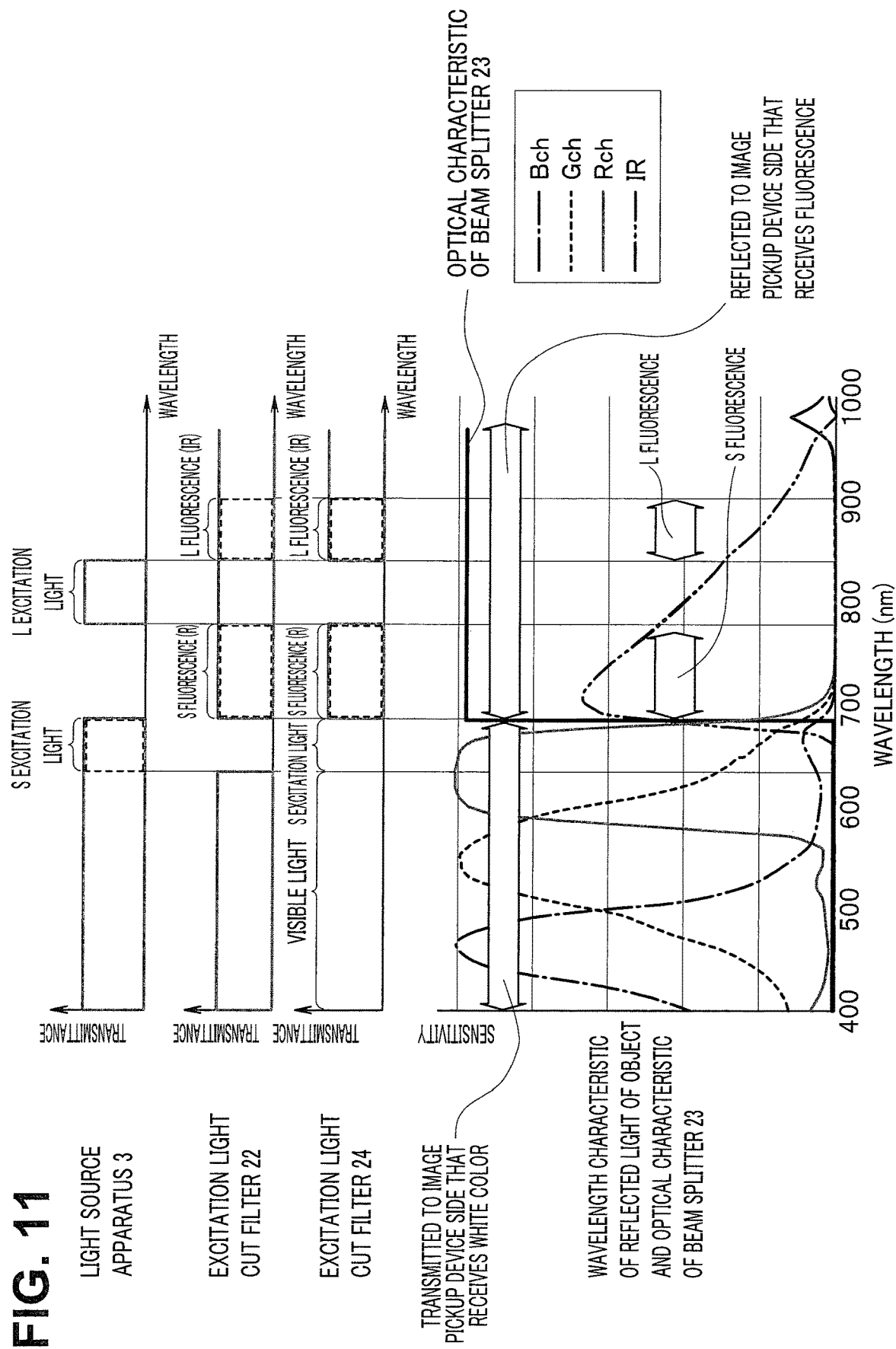
FIG. 11 is an explanatory diagram illustrating filter control of light in the example of the pattern A-d.

FIG. 10 and FIG. 11 are described using the same description method as in FIG. 2 and FIG. 3 respectively, and FIG. 10 and FIG. 11 are intended to describe light passing through the excitation light cut filters 22 and 24 and the beam splitter 23 in a pattern A-d. As shown in FIG. 11, in the pattern A-d, both S excitation light and L excitation light have a longer wavelength than that of visible light. Note that the wavelength band of S excitation light is a band on a longer wavelength side contiguous to the wavelength band of visible light. The return light from the object surface 61 includes white light, L excitation light and S excitation light, L fluorescence and S fluorescence. As shown in FIG. 11, red S fluorescence (R) is generated on a longer wavelength side of S excitation light and L fluorescence (IR) in the near-infrared band is generated on a longer wavelength side of L excitation light.

The return light from the object is made incident on the excitation light cut filter 22. In this case, the excitation light cut filter 22 is constructed of a single notch filter having a notch characteristic in the wavelength band of S excitation light, and removes the S excitation light component from the incident light and passes other wavelength bands. Thus, in this case, light including white light, L excitation light and L fluorescence and S fluorescence passes through the excitation light cut filter 22 and is made incident on the beam splitter 23.

As shown in FIG. 11, the beam splitter 23 passes a wavelength band of visible light and a wavelength band including the wavelength band of S excitation light and reflects other bands. White light made up of visible light and S excitation light is made incident on the image pickup device 25 in this way.

On the other hand, the beam splitter 23 changes the optical axis of visible light and the light other than the wavelength band of S excitation light by 90 degrees and emits the light to the excitation light cut filter 24. As shown in FIG. 11, in this case, the excitation light cut filter 24 cuts visible light and the wavelength band including S excitation light and L excitation light and passes a wavelength band of red S fluorescence (R), a wavelength band of L fluorescence (IR) of the near-infrared band, and a wavelength band on a longer wavelength side than L fluorescence (IR) of the near-infrared band. That is, the light that passes through the excitation light cut filter 24 is red S fluorescence (R) and a wavelength band equal to or longer than L fluorescence (IR) of the near-infrared band. Thus, S fluorescence and L fluorescence are made incident on the image pickup device 26.

Thus, in the pattern A-d, the light incident on the excitation light cut filter 24 is outgoing light of the beam splitter 23 that separates and reflects visible light and a wavelength band other than S excitation light, and the light from which visible light is cut is made incident on the excitation light cut filter 24 from the beam splitter 23. Furthermore, the excitation light cut filter 24 is configured to pass only red S fluorescence (R), L fluorescence (IR) of the near-infrared band, and a wavelength band having a longer wavelength than L fluorescence (IR) of the near-infrared band, and the excitation light cut filter 24 cuts visible light. Thus, visible light is cut by both filters of the beam splitter 23 and the excitation light cut filter 24, and the excitation light cut filter 24 emits light from which the visible light (white light) component is sufficiently removed. Thus, the fluorescence image obtained by the image pickup device 26 includes no white light component, and it is thereby possible to obtain a high accuracy fluorescence image.

In this way, the spectroscopic section in the present embodiment passes the wavelength band of visible light and reflects wavelength bands other than the passed wavelength band. A first excitation light cut filter is disposed between the object and the spectroscopic section on an optical path from the object to the image pickup device for white light observation via the spectroscopic section. The first excitation light cut filter cuts at least one wavelength band of two types of excitation light generating two types of fluorescence in a simultaneous observation mode in which white light observation and two types of fluorescence observation are performed simultaneously. The light reflected from the spectroscopic section includes neither the wavelength band of visible light cut by the spectroscopic section nor the wavelength band of excitation light cut by the first excitation light cut filter. Furthermore, the light reflected from the spectroscopic section is made incident on the image pickup device for fluorescence observation via a second excitation light cut filter configured to cut the wavelength band of the excitation light and the wavelength band of visible light not removed by the first excitation light cut filter. Of the light incident on the image pickup device for fluorescence observation, two types of excitation light are cut by the first and second excitation light cut filters and visible light is cut by the spectroscopic section and the second excitation light cut filter. That is, visible light is cut by the two filters of the spectroscopic section and the second excitation light cut filter, and then made incident on the image pickup device for fluorescence observation and it is possible to perform high accuracy fluorescence observation unaffected by white light.

Note that depending on a relationship between wavelength bands of two types of excitation light and two types of fluorescence and the wavelength band of visible light, the first excitation light cut filter may be constructed of a single notch filter and the second excitation light cut filter may be constructed of a long pass filter. In this case, it is possible to adopt a filter having a smaller number of films as the filter for cutting two types of excitation light and thereby improve manufacturing yield.

Second Embodiment

Figure 12:
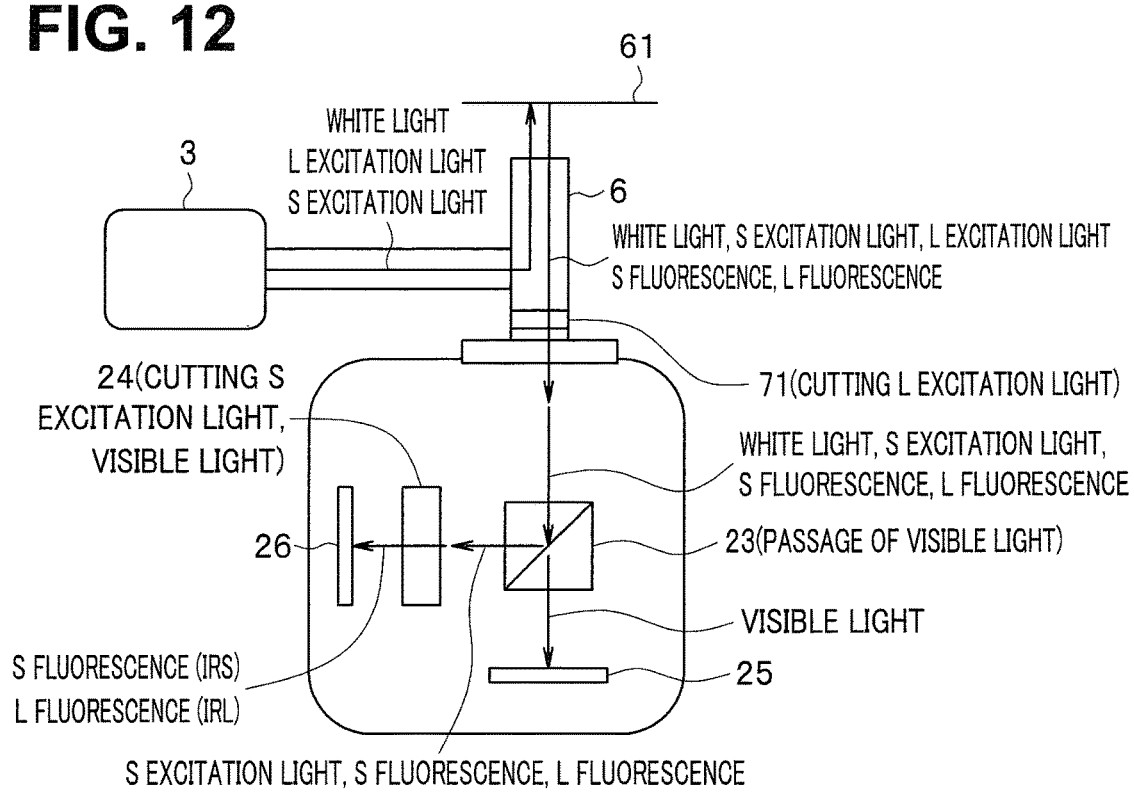
FIG. 12 is an explanatory diagram illustrating a second embodiment of the present invention.

FIG. 12 is an explanatory diagram illustrating a second embodiment of the present invention. In FIG. 12, components identical to the components in FIG. 2 are assigned identical reference numerals and description is omitted. FIG. 12 illustrates the second embodiment using the same description method as in FIG. 2. While FIG. 12 shows an example corresponding to the pattern A-d, the second embodiment is likewise applicable to the other aforementioned patterns as well.

The present embodiment is different from the first embodiment only in that an excitation light cut filter 71 is adopted instead of the excitation light cut filter 22 and other components are similar to the components in FIG. 1A. It is only the arrangement position that the excitation light cut filter 71 is different from the excitation light cut filter 22. The excitation light cut filter 71 is disposed in the optical viewing tube 2A on an optical path until return light is made incident on the beam splitter 23, has a characteristic similar to the characteristic of the excitation light cut filter 22, removes at least one of S excitation light and L excitation light from the return light and passes wavelength band components other than the removed wavelength band.

Other components and operations are similar to the components and operations of the first embodiment. The present embodiment can obtain effects similar to the effects of the first embodiment and when using the optical viewing tube 2A including an excitation light cut filter, the present embodiment provides an advantage that one excitation light filter can be omitted from the camera unit 2B.

Third Embodiment

Figure 13:
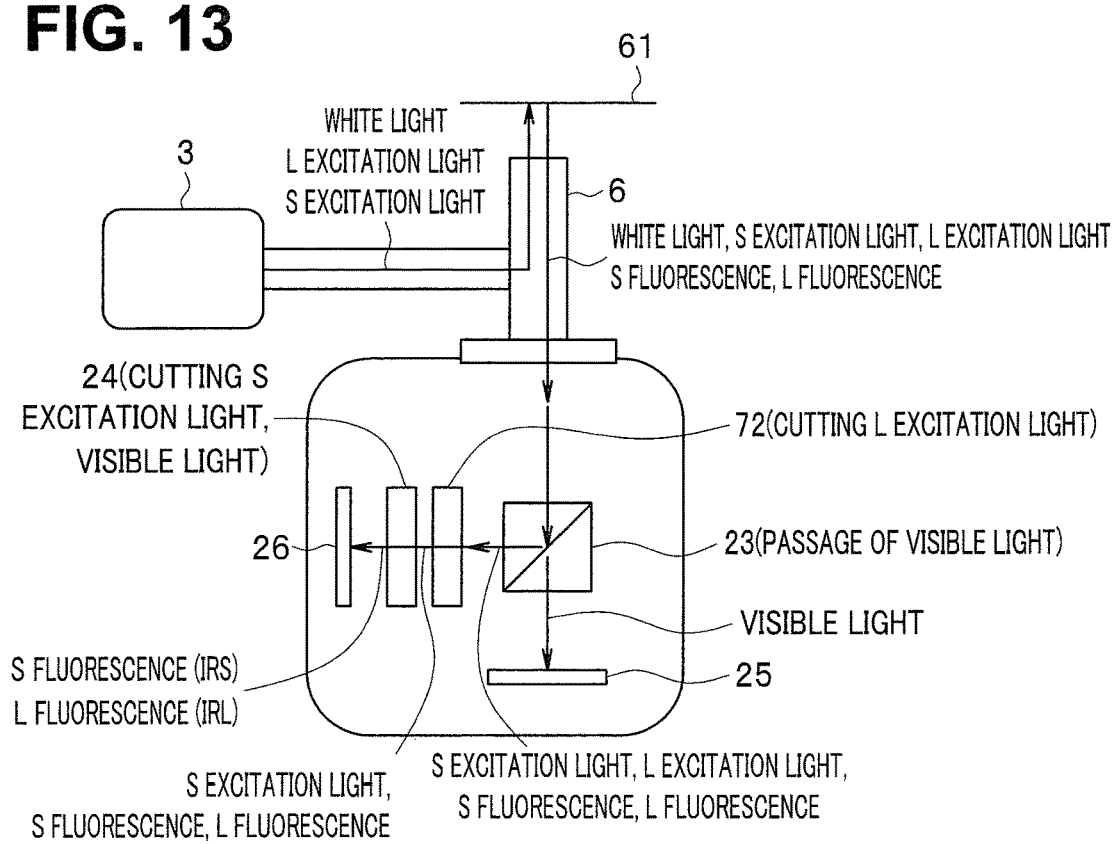
FIG. 13 is an explanatory diagram illustrating a third embodiment of the present invention.

FIG. 13 is an explanatory diagram illustrating a third embodiment of the present invention. In FIG. 13, components identical to the components in FIG. 2 are assigned identical reference numerals and description is omitted. FIG. 13 illustrates the third embodiment using the same description method as in FIG. 2. While FIG. 13 shows an example corresponding to the pattern A-d, the third embodiment is likewise applicable to the other aforementioned patterns as well.

The present embodiment is different from the first embodiment only in that an excitation light cut filter 72 is adopted instead of the excitation light cut filter 22 and other components are similar to the components in FIG. 1A. It is only the arrangement position that the excitation light cut filter 72 is different from the excitation light cut filter 22. The excitation light cut filter 72 is disposed on an optical path between the beam splitter 23 and the excitation light cut filter 24. The excitation light cut filter 24 has a characteristic similar to the characteristic of the excitation light cut filter 22, removes at least one of the wavelength bands of S excitation light and L excitation light from the outgoing light of the beam splitter 23 and passes wavelength band components other than the removed wavelength band.

Other components and operations are similar to the components and operations of the first embodiment. In the present embodiment, the return light from the object surface 61 passes through the beam splitter 23, the excitation light cut filter 72 and the excitation light cut filter 24 and is made incident on the image pickup device 26, and so the light incident on the image pickup device 26 is similar to the incident light of the first embodiment. Therefore, the present embodiment can also achieve effects similar to the effects of the first embodiment.

In the above-described embodiments, the optical section 21, the image pickup devices 25 and 26 and the signal processing circuit 27 are provided in the camera unit 2B, but the optical section 21, the image pickup devices 25 and 26 and the signal processing circuit 27 may also be provided in the elongated insertion portion which is inserted into the subject instead. The optical section 21, the image pickup devices 25 and 26 and the signal processing circuit 27 can be arranged even at the distal end portion, the proximal end portion or the intermediate portion as long as the parts are located within the insertion portion. Furthermore, the insertion portion may also be a flexible tube type including a bending portion. In all the above-described cases, the present embodiment has effects similar to the effects of the first, second and third embodiments.

The present invention is not limited to the above-described embodiments as they are, but can be implemented by modifying the components of the present invention without departing from the spirit and scope of the present invention in an implementation phase. Moreover, various types of inventions can be formed by combining a plurality of components disclosed in the above-described embodiments as appropriate. For example, some components may be deleted from among all the components disclosed in the embodiments. Furthermore, components among different embodiments may be combined as appropriate.

What is claimed is:

1. An endoscope apparatus comprising:
a beam splitter disposed on an optical axis of return light from an object irradiated with visible light, first excitation light and second excitation light, the second excitation light including a longer wavelength than a wavelength of the first excitation light, the beam splitter being configured to:
separate light of a first wavelength band including a wavelength band of the visible light,
make the light of the first wavelength band incident on an image pickup device for white light observation, and
separate and emit light of a second wavelength band other than the first wavelength band;
a first excitation light cut filter disposed on the optical axis between the object and the beam splitter, the first excitation light cut filter being configured to:
block a wavelength band of one of the first excitation light and the second excitation light included in the return light, and
emit the return light of a wavelength band other than the blocked wavelength band to the beam splitter; and
a second excitation light cut filter disposed on an optical axis of the light of the second wavelength band emitted from the beam splitter, the second excitation light cut filter being configured to:
block a wavelength band of another excitation light of the first excitation light and the second excitation light and the wavelength band of the visible light,
simultaneously pass light of a wavelength band of first fluorescence excited by the first excitation light and light of a wavelength band of second fluorescence excited by the second excitation light, and
emit light of a wavelength band other than the blocked wavelength bands to an image pickup device for fluorescence observation.

2. The endoscope apparatus according to claim 1, wherein the first excitation light cut filter comprises a single notch filter configured to block only the second excitation light, and
the second excitation light cut filter comprises a long pass filter configured to pass an entire band of wavelengths longer than the wavelength band of the first fluorescence.

3. The endoscope apparatus according to claim 1, wherein the first fluorescence is blue, green or red, and
the second fluorescence includes a longer wavelength than a wavelength of the visible light.

4. The endoscope apparatus according to claim 1, wherein none of the wavelength band of the first excitation light and the wavelength band of the second excitation light is included in the first wavelength band.

5. The endoscope apparatus according to claim 1, wherein one of the wavelength band of the first excitation light and the wavelength band of the second excitation light is included in the first wavelength band.

6. An endoscope apparatus comprising:
a beam splitter disposed on an optical axis of return light from an object, the beam splitter being configured to:
separate light of a first wavelength band including a wavelength band of visible light and make the light of the first wavelength band incident on an image pickup device for white light observation, and
separate light of a second wavelength band other than the first wavelength band and emit the light of the second wavelength band in a direction different from a direction of the optical axis;
a first excitation light cut filter disposed on the optical axis between the object and the beam splitter, the first excitation light cut filter being configured to:
block a wavelength band of at least one of first excitation light and second excitation light included in the return light, and
emit the return light of a wavelength band other than the blocked wavelength band to the beam splitter; and
a second excitation light cut filter disposed on an optical axis of the light of the second wavelength band emitted from the beam splitter, the second excitation light cut filter being configured to:
block a wavelength band of excitation light not blocked by the first excitation light cut filter of the first excitation light and the second excitation light, and a wavelength band of the visible light, and
emit light of a wavelength band other than the blocked wavelength band to an image pickup device for fluorescence observation,
wherein the second excitation light includes a longer wavelength than a wavelength of the first excitation light,
the first excitation light and first fluorescence generated from the object based on the first excitation light are included in the wavelength band of the visible light,
the second excitation light and second fluorescence generated from the object based on the second excitation light include longer wavelengths than a wavelength of the visible light,
the first excitation light cut filter blocks the wavelength bands of the first excitation light and the second excitation light, and
the second excitation light cut filter passes a longer wavelength band than a wavelength band of the first fluorescence, a wavelength band of the second fluorescence, and a wavelength band of the second fluorescence.

7. An endoscope apparatus comprising:
a beam splitter disposed on an optical axis of return light from an object, the beam splitter being configured to:
separate light of a first wavelength band including a wavelength band of visible light and make the light of the first wavelength band incident on an image pickup device for white light observation, and
separate light of a second wavelength band other than the first wavelength band and emit the light of the second wavelength band in a direction different from a direction of the optical axis;
a first excitation light cut filter disposed on the optical axis between the object and the beam splitter, the first excitation light cut filter being configured to:
block a wavelength band of at least one of first excitation light and second excitation light included in the return light, and
emit the return light of a wavelength band other than the blocked wavelength band to the beam splitter; and
a second excitation light cut filter disposed on an optical axis of the light of the second wavelength band emitted from the beam splitter, the second excitation light cut filter being configured to:

block a wavelength band of excitation light not blocked by the first excitation light cut filter of the first excitation light and the second excitation light, and a wavelength band of the visible light, and emit light of a wavelength band other than the blocked wavelength bands to an image pickup device for fluorescence observation, wherein the second excitation light includes a longer wavelength than a wavelength of the first excitation light, the first excitation light and first fluorescence generated from the object based on the first excitation light are included in the wavelength band of the visible light, the second excitation light and second fluorescence generated from the object based on the second excitation light include a longer wavelength than a wavelength of the visible light, the first excitation light cut filter blocks the wavelength band of the first excitation light, and the second excitation light cut filter passes a longer wavelength band than a wavelength band of the first fluorescence, a wavelength band of the second fluorescence, and a wavelength band of the second fluorescence.

8. An endoscope apparatus comprising:

a beam splitter disposed on an optical axis of return light from an object, the beam splitter being configured to:

separate light of a first wavelength band including a wavelength band of visible light and make the light of the first wavelength band incident on an image pickup device for white light observation, and separate light of a second wavelength band other than the first wavelength band and emit the light of the second wavelength band in a direction different from a direction of the optical axis;

a first excitation light cut filter disposed on the optical axis between the object and the beam splitter, the first excitation light cut filter being configured to:

block a wavelength band of at least one of first excitation light and second excitation light included in the return light, and emit the return light of a wavelength band other than the blocked wavelength band to the beam splitter; and a second excitation light cut filter disposed on an optical axis of the light of the second wavelength band emitted from the beam splitter, the second excitation light cut filter being configured to:

block a wavelength band of excitation light not blocked by the first excitation light cut filter of the first excitation light and the second excitation light and a wavelength band of the visible light, and emit light of a wavelength band other than the blocked wavelength band to an image pickup device for fluorescence observation, wherein the second excitation light includes a longer wavelength than a wavelength of the first excitation light, the first excitation light is included in the wavelength band of the visible light, first fluorescence generated from the object based on the first excitation light, the second excitation light and second fluorescence generated from the object based on the second excitation light include longer wavelengths than a wavelength of the visible light, the first excitation light cut filter blocks the wavelength band of the first excitation light, and the second excitation light cut filter passes a longer wavelength band than a wavelength band of the first fluorescence, a wavelength band of the second fluorescence, and a wavelength band of the second fluorescence.

* * * * *